United States Patent
Reid et al.

(10) Patent No.: US 9,370,187 B2
(45) Date of Patent: Jun. 21, 2016

(54) SELENIUM-BASED BIOCIDAL FORMULATIONS AND METHODS OF USE THEREOF

(71) Applicant: Selenium, Ltd., Austin, TX (US)

(72) Inventors: Ted W. Reid, Lubbock, TX (US); Julian Spallholz, Lubbock, TX (US); Robert Eugene Hanes, Austin, TX (US)

(73) Assignee: Selenium, LTD., Austin, TX (US)

( * ) Notice: Subject to any disclaimer, the term of this patent is extended or adjusted under 35 U.S.C. 154(b) by 617 days.

(21) Appl. No.: 13/762,147

(22) Filed: Feb. 7, 2013

(65) Prior Publication Data

US 2013/0165595 A1 Jun. 27, 2013
US 2016/0135463 A9 May 19, 2016

Related U.S. Application Data

(63) Continuation-in-part of application No. 12/699,440, filed on Feb. 3, 2010, now abandoned, and a continuation-in-part of application No. 13/704,899, filed as application No. PCT/US2011/040949 on Jun. 17, 2011, now abandoned.

(60) Provisional application No. 61/149,658, filed on Feb. 3, 2009, provisional application No. 61/149,650, filed on Feb. 3, 2009, provisional application No. 61/355,942, filed on Jun. 17, 2010.

(51) Int. Cl.

| | | |
|---|---|---|
| *A01N 55/00* | (2006.01) | |
| *A61K 31/095* | (2006.01) | |
| *A01N 25/10* | (2006.01) | |
| *A61K 9/00* | (2006.01) | |
| *A61L 15/46* | (2006.01) | |
| *A61K 31/26* | (2006.01) | |
| *A61K 31/655* | (2006.01) | |
| *A61K 33/04* | (2006.01) | |

(52) U.S. Cl.
CPC ............... *A01N 55/00* (2013.01); *A01N 25/10* (2013.01); *A61K 9/0014* (2013.01); *A61K 9/0051* (2013.01); *A61K 31/095* (2013.01); *A61K 31/26* (2013.01); *A61K 31/655* (2013.01); *A61K 33/04* (2013.01); *A61L 15/46* (2013.01); *A61L 2300/102* (2013.01); *A61L 2300/404* (2013.01)

(58) Field of Classification Search
None
See application file for complete search history.

(56) References Cited

U.S. PATENT DOCUMENTS

| | | |
|---|---|---|
| 3,202,690 A | 8/1965 | Previc |
| 4,166,820 A | 9/1979 | Spallholz et al. |
| 4,341,757 A | 7/1982 | Spallholz et al. |
| 4,496,559 A | 1/1985 | Henderson et al. |
| 4,512,977 A | 4/1985 | Lundy |
| 4,729,986 A | 3/1988 | Olson |
| 5,408,022 A | 4/1995 | Imazato et al. |
| 5,644,798 A | 7/1997 | Shah |
| 5,707,929 A | 1/1998 | Kuusisto et al. |
| 5,721,241 A | 2/1998 | el Kouni et al. |
| 5,783,454 A | 7/1998 | Spallholz et al. |
| 5,894,042 A | 4/1999 | Ferralli |
| 5,994,151 A | 11/1999 | Spallholz et al. |
| 6,033,917 A | 3/2000 | Spallholz et al. |
| 6,040,197 A | 3/2000 | Spallholz et al. |
| 6,043,098 A | 3/2000 | Spallholz et al. |
| 6,043,099 A | 3/2000 | Spallholz et al. |
| 6,077,714 A | 6/2000 | Spallholz et al. |
| 6,267,590 B1 | 7/2001 | Barry et al. |
| 6,673,385 B1 | 1/2004 | Ding et al. |
| 2002/0177863 A1 | 11/2002 | Mandel et al. |
| 2005/0008676 A1 | 1/2005 | Qiu et al. |
| 2007/0224275 A1 | 9/2007 | Reid et al. |
| 2008/0031931 A1 | 2/2008 | Gunn |
| 2010/0158966 A1 | 6/2010 | Reid et al. |
| 2010/0158967 A1 | 6/2010 | Reid et al. |

FOREIGN PATENT DOCUMENTS

| | | |
|---|---|---|
| DE | 210516 | 6/1984 |
| JP | 58057306 | 11/1988 |
| JP | 4108705 | 4/1992 |
| JP | 4120055 | 4/1992 |
| WO | WO 95/31218 | 5/1995 |
| WO | WO 00/49868 | 8/2000 |
| WO | WO 00/67762 | 11/2000 |
| WO | WO 2011160060 A2 * | 12/2011 |

OTHER PUBLICATIONS

Changez et al. Biomaterials 25, p. 139-146, 2004.*
Translation of FLS, Inc. of DD210516, original publication date May 1984.
Deidda, et al.; Pharmacological Research 36(3):193-197 (1997).
Rosa R M, et al. "Genotoxicity of diphenyl diselenide in bacteria and yeast" Mutation Search, Genetic Toxicology and Environmental Mutagenesis, Elsevier, Amsterdam, NL, vol. 563, No. 2, Oct. 10, 2004, pp. 107-115.
Yshivtsev, et al.; "Chalcogen-containing Analogs of Ehtylene Glycol and its Derivatives"; Russian Journal of General Chemistry; (2008); vol. 78, No. 4; pp. 608-613.
Sureshkumar, et al.; "Conformationally Locked Bridged Bicyclic Diselendies: Synthesis, Structure, Se-O Interaction and Theoretical Studies"; Journal of Organic Chemistry, (2007); vol. 72, pp. 5313-5319.
Beld, et al.; "Selenoglutathione: Efficient Oxidative Protein Folding by a Diselenide"; Biochemistry; (2007); vol. 46; pp. 5382-5390.
U.S. Appl. No. 13/704,899, Robert Eugene Hanes; Office Action, dated Dec. 2, 2014.

* cited by examiner

*Primary Examiner* — Nissa Westerberg
(74) *Attorney, Agent, or Firm* — Dunlap Codding, P.C.

(57) ABSTRACT

Biocidal compositions containing organoselenium compounds are disclosed, as well as methods of producing and using same.

15 Claims, 15 Drawing Sheets
(14 of 15 Drawing Sheet(s) Filed in Color)

Mechanical Properties of Polypropylene Loaded with Seldox Technology at Different Percentages

FIGURE 14
PP MB3 PP 10% Seldox_1% Se
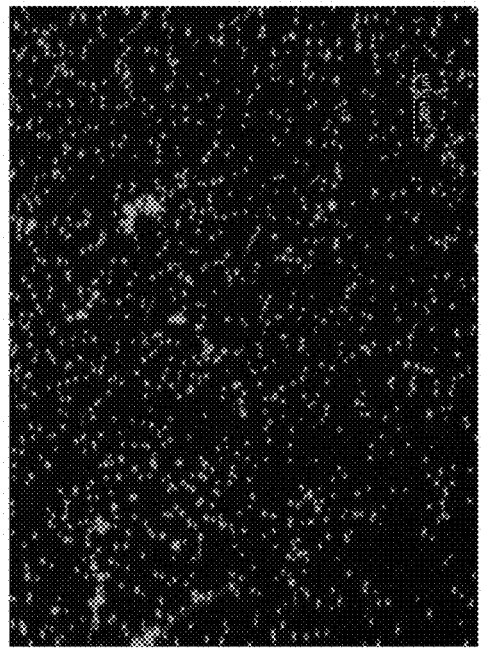
Control PP for MB3

SELENIUM-BASED BIOCIDAL FORMULATIONS AND METHODS OF USE THEREOF

CROSS REFERENCE TO RELATED APPLICATIONS/INCORPORATION BY REFERENCE STATEMENT

This application is a continuation-in-part of U.S. Ser. No. 12/699,440, filed Feb. 3, 2010, now abandoned; which claims benefit under 35 U.S.C. 119(e) of provisional applications U.S. Ser. No. 61/149,658, filed Feb. 3, 2009; and U.S. Ser. No. 61/149,650, filed Feb. 3, 2009. This application is also a continuation-in-part of U.S. Ser. No. 13/704,899, filed Jun. 17, 2011, now abandoned; which claims benefit under 35 U.S.C. 119(e) of provisional application U.S. Ser. No. 61/355,942, filed Jun. 17, 2010. The entire contents of each of the above-referenced patents and patent applications are hereby expressly incorporated herein by reference.

STATEMENT REGARDING FEDERALLY SPONSORED RESEARCH OR DEVELOPMENT

Not Applicable.

BACKGROUND OF THE INVENTION

1. Field of the Inventive Concept(s)

The presently disclosed and claimed inventive concept(s) relates generally to biocidal formulations that utilize free radical generation as a mechanism of toxicity, and more specifically, to selenium-based formulations that utilize free radical generation as a mechanism of toxicity.

2. Description of the Background Art

Selenium (Se) is among the most toxic of all known minerals. Throughout the period of time between the discovery of selenium toxicity in livestock in 1934 and 1988, many hypotheses were put forth to explain the mechanism by which many but not all compounds of selenium were toxic. None of these theories of selenium toxicity proved satisfactory in fully explaining why selenium was toxic. In 1989, Seko et al. (In: *Proceedings of the fourth international symposium on selenium and medicine* (ed., Wendel, A.) pp. 70-73, Springer-Verlag, Heidelberg, Germany, (1989)), reported that selenite, ($SeO_3$), an inorganic form of Se, reacted with a thiol, glutathione, (GSH), to produce superoxide ($O_2^-$). Since superoxide is a known toxicant, this raised the possibility that all selenium compounds that are toxic might generate superoxide. Through the testing of many selenium compounds, it was found that the inorganic compounds, $SeO_3$ and selenium dioxide ($SeO_2$) were able to generate $O_2^-$ and hydrogen peroxide ($H_2O_2$) when presented with a thiol, such as glutathione, cysteine (CysSH), or dithiothreitol $D(SH)_2$. Furthermore, it was found that all diselenides tested of the composition RSeSeR likewise would generate $O_2^-$ and $H_2O_2$ when presented with any of the before mentioned thiols.

In 1947, Feigl et al. (*Analytical Chemistry*, 19:351-353 (1947)), reported that selenium could catalyze a redox reaction involving sulfide oxidation. This soon became a common test for selenium using methylene blue. This reaction was further studied by others using different selenium compounds and thiols, demonstrating catalysis for some but not all selenium compounds. See, West et al. (*Analytic Chemistry*, 40:966-968 (1968)); Levander et al. (*Biochemistry*, 12:4591-4595 (1973)); Rhead et al. (Bioorganic Chemistry, 3:225-242 (1974)). The selenium catalytic activity of selenocystine (RSeSeR) in the presence of thiols was reported in 1958. It is now believed that all of the foregoing reactions of selenium compounds produce superoxide. See, Xu et al. (*Advances in Free Radical Biology and Medicine*, 1:35-48 (1991)); Xu et al. (*Huzahong Longong Daxus Xuebao*, 19:13-19 (1991)); Kitahara et al. (*Archives of toxicology*, 67:497-501 (1993)); Chaudiere et al. (*Archives of Biochemistry and Biophysics*, 296:328-336 (1992)).

Selenium and a number of its compounds have been known since the early 1970's to possess anti-cancer properties. It has been generally recognized that selenite and selenium dioxide are good anti-cancer agents in vitro and in experimental animals and that the compounds are also cytotoxic to both cancer and normal cells in vitro. U.S. Pat. No. 5,104,852 issued to Kralick et al. describes the use of selenodiglutathione (GSSeSG) and other selenodithiols of the configuration (RSSeSR) to treat cancer. Selenodiglutathione is the product of the reaction between selenite or selenium dioxide with glutathione. The compound, selenodiglutathione, has been isolated. U.S. Pat. No. 5,104,852, however, does not describe the mechanism of action by which selenodiglutathione and like compounds are useful in treating cancer.

In 1982, the interaction of selenite and selenocystine with glutathione in the cytotoxicity and lysis of rat erythrocyte membranes was described by Hu et al. (*Biochemical Pharmacology*, 32:857-961 (1983)). This cytotoxicity, as revealed by scanning electron microscopy of rat erythrocytes, caused the erythrocyte membranes to become burred, the cells to quadruple in size and lyse similar to that described by Kellogg et al. (*J. Biol. Chem.*, 252:6721-6728 (1977)). This toxicity, however, was not expressed by selenomethionine, a compound possessing the configuration $RSeCH_3$. In 1991, an article by Yan et al. (*FASEB J.*, 5:A581 (1991)), showed a dose responsive toxicity of several selenium compounds to a human mammary tumor cell line. Additional investigations using lucigenin chemiluminescence and luminol chemiluminescence revealed a dose response in $O_2^-$ and $H_2O_2$ generated chemiluminescence by selenite, selenium dioxide and all selenium compounds tested of the configuration RSeSeR. Furthermore, it was found that selenium compounds in the presence of either tumor cells or glutathione alone produced superoxide and $H_2O_2$. Chemiluminescence from the reactions of lucigenin with $O_2^-$ or luminol with $H_2O_2$ could be quenched by the native enzymes superoxide dismutase (SOD), catalase (CT) or glutathione peroxidase (GSHPx). Denatured enzymes would not quench these reactions, confirming the generation of the free radical ($O_2^-$) and $H_2O_2$ by selenium compounds and thiols. All of this selenium free radical chemistry has been reviewed by Spallholz (*Free Radical Biology and Medicine*, 17:45-64, (1994)).

A summation of this large body of experimental data on selenium toxicity, catalysis and carcinostatic activity is as follows:

1) The selenium compounds, $SeO_2$ and $SeO_3$, react with thiols to produce a selenodithiol of the configuration (RSSeSR). This compound is not toxic per se nor is it carcinostatic. The toxic carcinostatic form of RSSeSR is the reduced selenide anion, $RSSe^-$. This selenopersulfide form of Se is catalytic as shown by the inhibition of both catalysis and superoxide generation by iodoacetic acid and mercaptosuccinic acid.

2) Selenium compounds of the configuration (RSeSeR) or (RSeSeR') react with thiols to produce the reduced selenite anion $RSe^-$ or $R'Se^-$. This selenide ionic form of Se is catalytic as shown by the inhibition of both catalysis and superoxide generation by iodoacetic acid and mercaptosuccinic acid.

3) Organic selenium catalysts of the configuration RSSe⁻, the selenopersulfide anion, is catalytic in the presence of thiols, and RSSe⁻ continues to generate superoxide ($O_2^-$) ion as long as sufficient concentrations of $O_2^-$ and thiol are in the medium. All of these selenium compounds derived from selenite or selenium dioxide reacting with glutathione (GSH) are converted to elemental selenium (Se.) as follows; $SeO_3$ ($SeO_2$)+ 2GSH→2GSSeSG→2GSSG+Se.. Elemental selenium (Se.) is non-catalytic and not toxic.

4) Compounds of selenium of the configuration RSe⁻ or RSSe⁻ are toxic due to the catalytic acceleration of thiol oxidation which produces $O_2^-$, $H_2O_2$ and the more toxic free radical, the hydroxyl radical (.OH). This chemistry had been discussed by Misra (*J. Biol. Chem.*, 249:2151-2155 (1974)) for the spontaneous oxidation of thiols. The association of rapid thiol catalysis by selenium compounds of the configuration RSe⁻ or RSSe⁻ and the toxicity from which it produced free radicals and reactive toxic oxygen products was recognized in 1992 by one of the inventors.

The use of selenium for the treatment of experimental cancer in animals and cancer in humans in vivo has been extensively described by many authors, such as Milner et al. ("Selenium and transplantable tumors," (Spallholz, J. E., Martin, J. L., Ganther, H. E., eds.) *Selenium in Biology and Medicine, AVI Publishing Co.* (1981)); Ip et al. ("Relationship between the chemical form of selenium and anticarcinogenic activity," CRC Press, Inc., pp. 479-488 (1992)); Caffrey et al. (*Cancer Research*, 52:4812-4816 (1992)); Schrauzer (*Biol. Trace Elem. Res.*, 33:51-62 (1992)); and Yan et al. (*Biochemical Pharmacology*, 45:429-437 (1993)). The use of selenium as a cytotoxic agent to both normal cells and cancer cells in vitro for the injection of selenodiglutathione into a tumor mass to kill tumor cells has been described in U.S. Pat. No. 5,104,852, issued to Kralick et al. In U.S. Pat. No. 4,671,958, Rodwell et al. described many antibacterial drugs, 3 antiviral drugs, 1 antifungal drug, 7 antineoplastic drugs, 3 radiopharmaceuticals, 3 heavy metals and 2 antimycoplasmals as drugs for antibody mediated delivery. The pharmacology for all of these drugs which are listed in Table 1 of U.S. Pat. No. 4,671,958 is generally understood. Table 1 of the Rodwell et al. patent does not contain selenium because its pharmacological action as a free radical generator of ($O_2^-$) and other reactive oxygen molecules was not understood or known at that time.

Humans and other animals are in a constant immune-system battle with agents of infectious disease, such as bacteria, viruses, pathogenic fungi and protozoa. A particular problem for healthcare professionals dealing with these infectious agents has been the development of antibiotic resistant bacteria, which are refractory to many of the antibiotic agents that initially promised to provide a reliable cure.

As a result of widespread public concern with infectious bacteria, antimicrobial treatment of materials such as fabrics, fibers, polymers and even children's toys have become increasingly popular. While the demand for such antimicrobial articles is high, relatively few types of such articles are available, and not all of those available are both effective against a broad spectrum of bacteria and capable of sustained antimicrobial activity without being released into the environment or being gradually chemically inactivated.

Research and development of durable functional fibers has advanced in recent years, including new methods of incorporating antibiotics as bactericidal agents directly into the fibers. The chemical and medical literature describes many compounds that have antimicrobial activity. Although the mechanism of action of these antimicrobials varies, they generally function by one or more of the following manners: inhibition of cell wall synthesis or repair; alteration of cell wall permeability; inhibition of protein synthesis; and/or inhibition of the synthesis of nucleic acids (DNA or RNA).

At least since the 1870s, silver ions have been recognized as an antibacterial agent, and have been particularly noted for their ability to resist the development of drug-resistance in target bacteria. In general, silver cations (Ag+) are thought to possess antimicrobial activity because they are highly reactive chemical structures that bind strongly to electron donor groups containing sulfur, oxygen, or nitrogen that are present in microbial targets. The biological target molecules generally contain all these components in the form of thio, amino, imidazole, carboxylate, and phosphate groups. Silver ions act by displacing other essential metal ions such as calcium or zinc. The direct binding of silver ions to bacterial DNA may also serve to inhibit a number of important transport processes, such as phosphate and succinate uptake, and can interact with cellular oxidation processes as well as the respiratory chain. The silver ion-induced antibacterial killing rate is directly proportional to silver ion concentrations, typically acting at multiple targets. Indeed, for silver ion-based antimicrobial articles and devices to be effective as antimicrobial vectors, the silver ions with which they are impregnated must be slowly released into the environment so that they are free to contact and inhibit the growth of destructive microbes in the environment. Accordingly, the antimicrobial activity of silver-coated and silver-impregnated articles and devices is dependent upon the controlled release rate of the unbound, free silver ions they carry, and the continued antimicrobial efficacy of such silver-based antimicrobials is necessarily limited by the supply of free silver ions they retain.

The inventor's previous work, as disclosed and claimed in U.S. Pat. Nos. 5,783,454; 5,994,151; 6,033,917; 6,040,197; 6,043,098; 6,043,099; and 6,077,714; all issued to Spallholz et al., discloses methods for making selenium-carrier conjugates by covalently attaching (i) an organic selenium compound selected from the group consisting of RSeH, RSeR', RSeSeR and RSeSeR', wherein R and R' each comprise an aliphatic residue containing at least one reactive group selected from the group consisting of aldehyde (ketone), amino, alcoholic, phosphate, sulfate, halogen, alkane, alkene, alkyne or phenolic reactive groups and combinations thereof, to (ii) a carrier having a constituent capable of forming a covalent bond with said reactive groups of said selenium compound to produce a selenium-carrier conjugate which is capable of specific attachment to a target site. The carrier may be a protein, such as an antibody specific to a bacteria, virus, protozoa, or cell antigen, including without limitation, cell surface antigens, a peptide, carbohydrate, lipid, vitamin, drug, lectin, plasmid, liposome, nucleic acid or a non-metallic implantable device, such as an intraocular implant or a vascular shunt.

The '454 patent demonstrates the cytotoxicity of selenofolate of the configuration Folate-SeR, which produces superoxide in the presence of glutathione or other thiols, as measured by lucigenin chemiluminescence; this modified vitamin compound is cytotoxic to cancer cells upon uptake in a dose dependent manner. The '454 patent also demonstrates the ability of selenocystamine attached to plastic or a cellulose matrix to inhibit cellular growth.

The selenium-carrier conjugates of the prior art (as taught in the various patents listed above) require covalent attachment of the selenium compound to the carrier molecule in order to be effective. In addition, the leaving groups generated when RSe— is produced, as taught by the prior art, are toxic.

Therefore there is a need for sustainable and effective biocidal agents that both avoid the formation of resistant microbes and can be adapted for use in manufacturing materials, and in application to solid substrates, which overcome the disadvantages and defects of the prior art. It is to such improved biocidal compositions, and methods of production and use thereof, that the presently disclosed and claimed inventive concept(s) is directed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 14 contains confocal laser scanning microscopic images visualizing any bacteria attached to the masterbatch contact lens case formed from another masterbatch resin dosed with the organoselenium compound.

DETAILED DESCRIPTION OF THE INVENTIVE CONCEPT(S)

Figure 1:
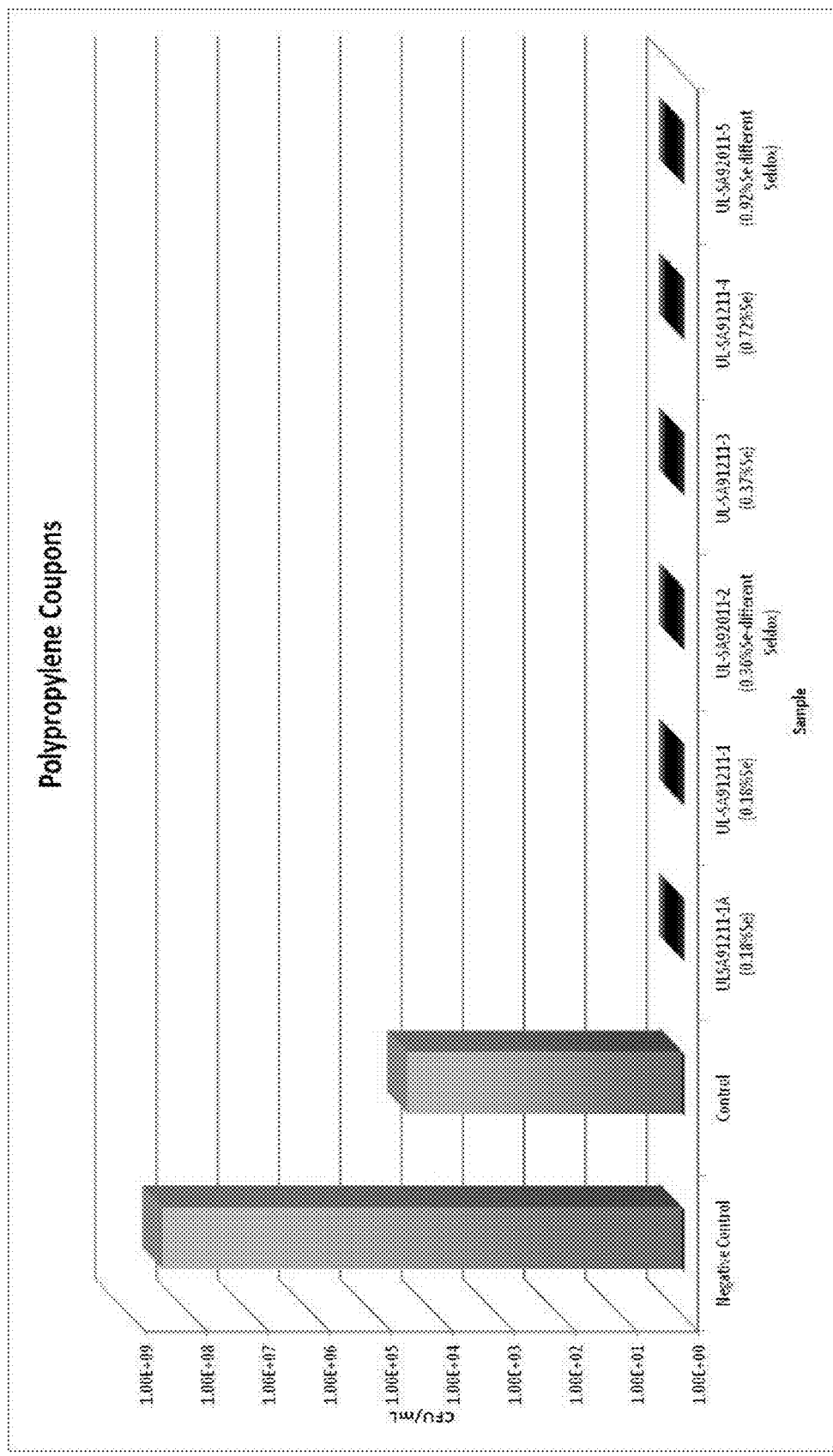
FIG. 1 graphically illustrates the effects of an organoselenium compound, diselanediylbis(2-hydroxypropane-3,1-diyl)bis(2-methylacrylate), on the proliferation of *Staphylococcus aureus* on various polypropylene coupons formed by extrusion of various thermoplastic resin pellets that had been mixed with the organoselenium compound.

Before explaining at least one embodiment of the presently disclosed and claimed inventive concept(s) in detail by way of exemplary drawings, experimentation, results, and laboratory procedures, it is to be understood that the presently disclosed and claimed inventive concept(s) is not limited in its application to the details of construction and the arrangement of the components set forth in the following description or illustrated in the drawings, experimentation and/or results. The presently disclosed and claimed inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual ($2^{nd}$ ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and claimed herein can be made and executed without undue experimentation in light of the present disclosure. While the compositions and methods of the inventive concept(s) have been described in terms of preferred embodiments, it will be apparent to those of skill in the art that variations may be applied to the compositions and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

"Treatment" refers to both therapeutic treatment and prophylactic or preventative measures. Those in need of treatment include those already with the disorder as well as those in which the disorder is to be prevented.

A "disorder" is any condition that would benefit from treatment with the compositions of the presently disclosed and claimed inventive concept(s). This includes chronic and acute disorders or diseases including those pathological conditions which predispose the mammal to the disorder in question.

"Mammal" for purposes of treatment refers to any animal classified as a mammal, including human, domestic and farm animals, nonhuman primates, and zoo, sports, or pet animals, such as dogs, horses, cats, cows, etc.

The terms "covalently attached", "covalent bonding" and "covalent attachment" as used herein will be understood to refer to a stable chemical link between two atoms produced by sharing of one or more pairs of electrons. Covalent bonding is an intramolecular form of chemical bonding characterized by the sharing of one or more pairs of electrons between two components, producing a mutual attraction that holds the resultant molecule together. Atoms tend to share electrons in such a way that their outer electron shells are filled. Such bonds are always stronger than the intermolecular hydrogen bond and similar in strength to or stronger than the ionic bond. In contrast to the ionic and metallic bond, the covalent bond is directional, i.e., the bond angles have a great impact on the strength of the bond. Because of the directional character of the bond, covalently bound materials are more difficult to deform than metals.

The terms "noncovalently attached", "noncovalent bonding", "noncovalent interactions" and "noncovalent attachment" as used in accordance with the presently disclosed and claimed inventive concept(s) will be understood to refer to any methods of attachment that do not involve a molecule-to-molecule covalent attachment. A noncovalent bond is a chemical bond in which, in contrast to a covalent bond, no electrons are shared. Noncovalent bonds are relatively weak, but they can sum together to produce strong, highly specific interactions between molecules.

Noncovalent bonding refers to a variety of interactions that are not covalent in nature between molecules or parts of molecules that provide force to hold the molecules or parts of molecules together, usually in a specific orientation or conformation. Specific examples of non-covalent interactions include, but are not limited to, ionic bonds, hydrophobic interactions, hydrogen bonds, Van der Waals forces (aka London dispersion forces), Dipole-dipole bonds, and the like.

"Noncovalent bonding", "Noncovalent interactions" and "Noncovalent forces" all refer to these forces as a whole without specifying or distinguishing which specific forces are involved because noncovalent interactions often involve several of these forces working in concert. Noncovalent bonds are weak by nature and must therefore work together to have a significant effect. In addition, the combined bond strength is greater than the sum of the individual bonds. This is because the free energy of multiple bonds between two molecules is greater than the sum of the enthalpies of each bond due to entropic effects.

The term "biocidal composition" as utilized herein refers to a chemical substance capable of killing different forms of living organisms. A biocidal composition can be a pesticide, such as but not limited to, fungicides, herbicides, insecticides, algicides, moluscicides, miticides, and rodenticides; or the biocide can be an antimicrobial, such as but not limited to, germicides, antibiotics, antibacterials, antivirals, antifungals, antiprotozoans, and antiparasites.

The term "plastics" as utilized in accordance with the presently disclosed and claimed inventive concept(s) refers to any of numerous substances that can be shaped and molded when subjected to heat or pressure. Plastics are easily shaped because they consist of long-chain molecules known as polymers, which do not break apart when flexed. Plastics are usually artificial resins but can also be natural substances, like celluloses, guars, xanthans, certain cellular derivatives, and shellac. Plastics can be pressed into thin layers, formed into objects, or drawn into fibers for use in textiles. Most do not conduct electricity well, are low in density, and are often very tough. Examples of plastics that may be utilized in accordance with the presently disclosed and claimed inventive concept(s) include, but are not limited to, polyvinyl chloride, methyl methacrylate, polystyrene, polyurethane, and the like. The term "plastics" as used herein will also be understood to include waxes.

The term "species of interest" as utilized in accordance with the presently disclosed and claimed inventive concept(s) refers to any living cell, virus or organism that is killed or suppressed when exposed to free radicals. The term "species of interest" includes, but is not limited to, prokaryotes such as bacteria and archebacteria; viruses; eukaryotes such as mold, fungi, protozoans, parasites, plant cells and animal cells; and biological materials such as proteins, carbohydrates, lipids and nucleotides. Examples of prokaryotes include, but are not limited to, bacteria such as for example, *Staphylococcus* strains such as but not limited to, *S. aureus*; *Pseudomonas* strains such as but not limited to, *P. aeruginosa*; *Escherichia* strains such as but not limited to, *E. coli*; and *Bacillus* strains such as but not limited to, *B. subtilis*. Examples of viruses include, but are not limited to, Poxvirus, Papillomavirus, Filovirus, Bornavirus, Mimivirus, Picornavirus, Adenovirus, Retrovirus, Paramyxovirus, Flavivirus, Parvovirus, Hepadnavirus, Calcivirus, and Orthomyxovirus and Bacteriophage; specific viral examples include HIV, Rhinovirus, West Nile, Influenza, smallpox, and herpes simplex. Examples of parasites include, but are not limited to, arthropod parasites, helminth parasites, protozoal parasites, and hematoprotozoal parasites; specific examples include demodex mange, hookworm, and coccidia. Examples of eukaryotic cells include, but are not limited to, fibroblast cells, barnacles, epithelial cells, and cancer cells, including but not limited to, prostate cancer cells, breast cancer cells, leukemia, and lymphoma.

Turning now to the presently disclosed and claimed inventive concept(s), the inventive concept(s) is based, in part, upon the finding that inorganic and organic selenium compounds, which catalyze the formation of free radical superoxide ions in the presence of oxygen and a reducing agent such as a reduced thiol group or other electron donor, have biocidal activity when brought into contact with a species of interest, such as but not limited to, bacteria, viruses, mold, fungi, protozoa parasites, plant cells, animal cells, biological materials and combinations thereof. While not wishing to be bound by a single theory of their mechanism of biocidal action, such selenium-containing compounds appear to provide for catalytic superoxide-mediated damage to a target species of interest by generating short-lived but highly reactive superoxide ($O_2-$) ions in the presence of oxygen ($O_2$) and reduced thiol groups (SH— groups) or other electron donating groups (i.e., cofactors such as but not limited to, NADPH in NADPH dependent reductase) present on the target species of interest itself (e.g., from membrane proteins or other reducing sources present on or near the target species). Accordingly, the presently disclosed and claimed inventive concept(s) provides novel selenium-based methods, formulations, and articles for the treatment and/or inhibition of the proliferation of infectious, disease-causing agents and other unwanted cells (including the formation of biofilms).

The presently disclosed and claimed inventive concept(s) is related to biocidal compositions comprising a selenium composition. Broadly, the biocidal compositions include at least one selenium atom that is capable of forming the species Se— and thus results in free radical generation that is damaging to any species of interest if the Se— is available to a surface of the species of interest in a proximity that allows for free radical catalysis to be performed. In addition to the selenium atom, the biocidal composition contains three functional groups, as described in greater detail herein below. In particular embodiments, the biocidal composition possesses the following formula:

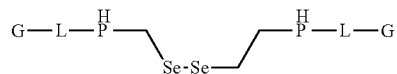

G = grafting agent
L = linker group
P = properties group wherein the grafting agent, the linker group, and the properties group represent the three functional groups of the biocidal composition. These three groups modulate properties of the biocidal composition to "fine tune" the biocidal composition and provide compatibility with a substrate on which the biocidal composition is disposed (such as, for example but not by way of limitation, a thermoplastic resin from which a substrate having the biocidal composition incorporated therein is formed, or a liquid substrate in which the biocidal composition is disposed).

The grafting agent is a first functional group that attaches the biocidal composition to the substrate. In certain embodiments, the grafting agent is selected from the group consisting of vinyl, acrylate, methacrylate, acrylamide, vinyl, alcohol, amine, carboxylic acid, ester, amide, ether, acid chloride, N-hydroxysuccinimide activated esters, and combinations thereof. The grafting agent may interact with a molten polymer from which a substrate is formed, or the grafting agent may graft to functional groups within a polymer or monomer composition from which a substrate is formed. In certain embodiments, the grafting agent covalently attaches the biocidal composition to the substrate.

The linker group is a second functional group that modulates solubility of the biocidal composition. The linker group is an organic group that may contain 2-20 carbons (such as but not limited to, 4-10 carbons), with the length of this group being dependent upon the end application. While the linker group is chosen for its solubilizing properties, it may also function to maximize the percentage of selenium in the biocidal compound. For example, the percentage of selenium in the biocidal composition may be in a range of from 15% to 60%, or 30% to 55%. In certain embodiments, the linker group is selected from the group consisting of linear aliphatic chains, branched aliphatic chains, ring structures, and combinations thereof. The ring structures may be aromatic, such as, but not limited to, benzene and toluene derivatives; these derivatives may be attached in certain embodiments through the 1 and 4 positions. However, when geometry of the structure is key to the application, the attachment points could be 1,2; 1,3; 1,5; 2,5; or any such combination that creates the preferred geometry to maximize the activity of the selenium atoms in the compositions. Aromatic rings may also be benzene, toluene, xylene, naphthalene or anthracene through attachment points. In the rings possessing 2 or more rings, the attachment points can be, for example but not by way of limitation, 1,8; 2,9; 2,7; and the like.

The linker group is chosen to provide compatibility with the material from which the substrate is formed (such as, but not limited to, a resin of choice). For example but not by way of limitation, when the substrate is produced from organic media ranging from solvents to polymers, the solubility of the linker group is chosen to maximize compatibility with this media (i.e., hydrophobic linker groups are utilized with hydrophobic resins). When the substrate is produced from more hydrophilic resins, the L group may possess additional functionality, such as, but not limited to, alcohol, amine or phenol groups, to aid in compatibility of the biocidal composition with the substrate.

The properties group is a third functional group that modulates physical properties of the biocidal composition, including but not limited to the boiling point, volatility, and/or solubility. In certain embodiment, the properties group is selected from the group consisting of alcohols, amines, carboxylic acids, and combinations thereof. For example but not by way of limitation, alcohol groups may be chosen to increase the boiling point; this modulated property makes the compound less volatile and aids in high temperature processing to minimize fumes of the resultant organoselenium species. In addition, the properties group may also act in concert with the linker group to modulate solubility.

Particular examples of biocidal compositions in accordance with the presently disclosed and claimed inventive concept(s) that possess the three functional groups and selenium compounds include, but not limited to, diselanediylbis (2-hydroxypropane-3,1-diyl)bis(2-methylacrylate) and 3,3'-diselanediylbis(propane-1,2-diol).

The presently disclosed and claimed inventive concept(s) includes a composition that comprises any of the biocidal compositions disclosed herein above, disposed on and/or attached to (including but not limited to, impregnated throughout and/or interdigitated within) a substrate. In certain embodiments, the substrate may be a solid substrate, such as but not limited to, a solid substrate formed from a thermoplastic polymer. The biocidal composition may be incorporated into a molten polymer (or otherwise mixed with the polymer) prior to formation of the solid substrate, whereby the biocidal composition may become impregnated throughout the solid substrate and permanently attached thereto such that the biocidal composition is substantially unable to leach from the solid substrate. For example but not by way of limitation, the grafting agent may thermally graft and thus covalently attach the biocidal composition to the molten polymer via free radicals generated by the molten polymer. The biocidal composition may be mixed with the thermoplastic polymer prior to extrusion of the material, during the extrusion process, or immediately following extrusion but prior to hardening of the thermoplastic polymer into the solid substrate. Alternatively, the biocidal composition may be applied to a surface of the solid substrate after the solid substrate is formed.

The term "molten plastic" as used herein will be understood to include not only a plastic that has been heated to the point that it is in a completely liquid form, but will also include plastic that has been heated sufficiently so that the plastic is softened (but not liquefied). Therefore, the term "molten plastic" encompasses heated plastics in both liquid as well as softened, semi-solid forms. This term particularly encompasses the family of thermoplastic and thermoset resins known to those of ordinary skill in the art, including but not limited to, polypropylene, polyethylene, polyolefins, polyurethanes, nylons, ABS, polyesters, and combinations thereof, as well as any of the additional thermoplastic and/or thermoset resins described herein below.

Alternatively, a non-heated form of plastic may be used to form the substrate. For example a liquid monomer may be mixed with the biocidal composition, followed by initiation of polymerization to form a mixed polymer that includes the biocidal composition described herein above, wherein the composition copolymerizes into the backbone or branches of the resulting polymer. In this manner, the biocidal composition may be distributed throughout the matrix material as the material hardens. When the biocidal composition is incorporated throughout said plastic material, the plastic material can wear; that is, the plastic material may slowly dissolve during use thereof, for example but not limited to, a polymer used as a knee implant); however, as the plastic material wears, selenium will still be continuously found on the surface of the plastic material.

Figure 15:
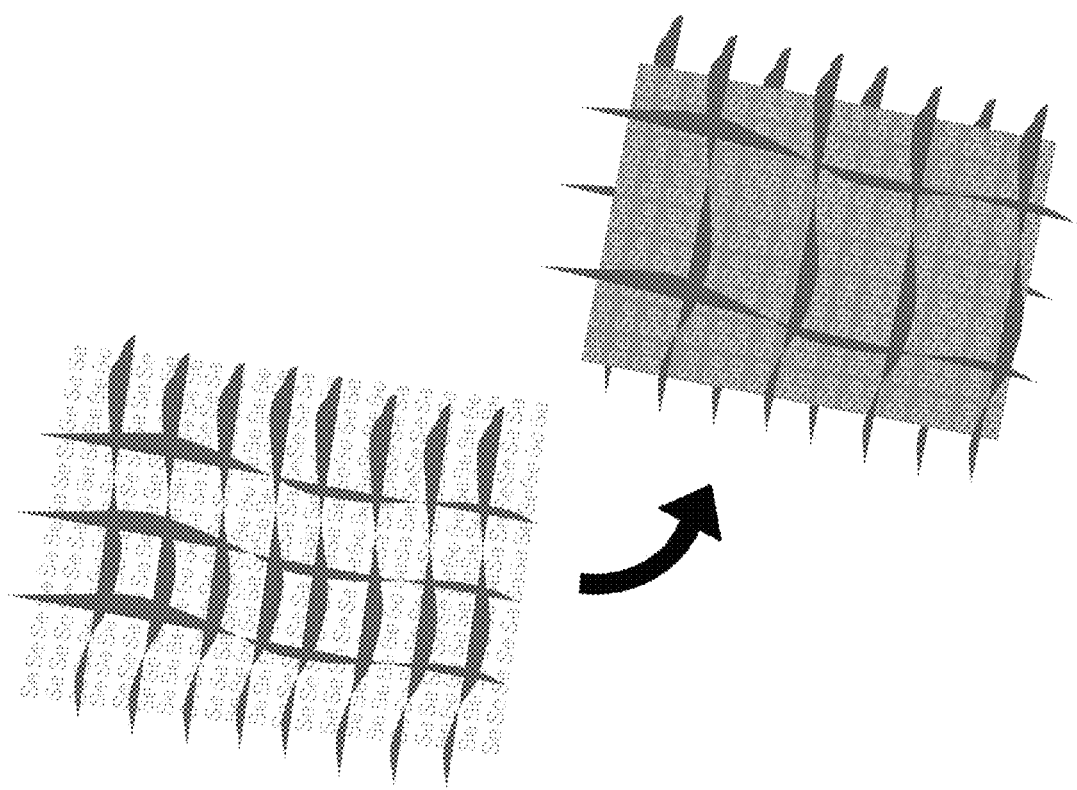
FIG. 15 contains a pictorial representation illustrating how a selenium grafting agent forms a covalent bonding backbone or branched polymer chains that are interwoven in open spaces of a substrate. In this manner, new covalent bonds are not formed between the substrate and the biocidal grafting agent; rather, the biocidal grafting agent is threaded as over/under threads through the empty spaces of the substrate.

In other embodiments, the substrate to which the biocidal composition is added may be a semi-permeable substrate. The biocidal composition disperses into the open spaces of the semi-permeable substrate, and the grafting agent of the biocidal composition interdigitates the semi-permeable substrate to form a covalent network within the semi-permeable substrate that is interwoven within the open spaces of the preexisting material. The biocidal composition may then be cured such that new covalent bonding backbone or branched polymer chains are interwoven in the open spaces of the preexisting material. In this manner, the biocidal composition becomes permanently attached to the semi-permeable substrate such that the biocidal composition is substantially unable to leach from the semi-permeable substrate; however, new covalent bonds may not be formed between the existing material and the biocidal grafting agent; rather, the biocidal grafting agent may simply be threaded as over/under threads through the empty spaces of the preexisting material to form the covalent network, as shown in FIG. 15. In this manner, the covalent network formed by the grafting agent may be substantially free of covalent bonds between the grafting agent and the semi-permeable substrate, such that the grafting agent is substantially not attached to the semi-permeable substrate; rather, the interdigitated branches of the covalent network permanently attach the covalent network to the semi-permeable substrate. Alternatively, the grafting agent may be covalently attached to the semi-permeable substrate.

Non-limiting examples of compounds from which the substrates can be formed include polypropylene, polyethylene, polyolefins, polyurethanes, thermoplastic polyurethanes (TPU), nylons, polyacrylates, polymethyl methacrylates, isoprenes, polytetrafluoroethylenes, fluoropolymers, polyacrylonitriles, butadiene styrenes, acrylonitrile butadiene styrenes (ABS), polyethylene terephthalates, polybutylene terephthalates, polyesters, polysulfenes, polysulfones, aromatic polysulfones, polyphenylene oxides, polyphenylene ethers, polyphenylene sulfides, polyphenylene sulfones, polyether sulfones, aromatic polyether sulfones, bisphenols, dichlorodiphenoxy sulfones, polyether ketones, aromatic polyether ketones, sulfonated polyether ketones, phenoxides (such as but not limited to, phenoxides made from epichlorohydrin and bisphenol A), polyvinylidene fluorides, sulfonated polyvinylidene fluorides, nylons, vinyl chloride homo-polymers, vinyl chloride co-polymers, polyvinyl chlorides, polyvinyl chloride/nitriles, vinyl acetates, ethylene vinyl acetates, poly butylenes, polybutylenes, chlorobutyls, polystyrenes, polycarbonates, polytetrafluoroethylenes, polyphtatamides, glass fibers, porous carbons, graphites, inorganic membranes based on alumina, silicas, silicones, cellulose acetates, epoxys, butyl rubbers, styrene butadiene rubbers, fluoropolymers, polyvinylpyrrolidones, and combinations and copolymers thereof.

Examples of aqueous and non-aqueous applications of the biocidal compositions of the presently disclosed and claimed inventive concept(s) are in particular, but not limited to, surface coatings, protective paints, and other coatings in the following: roofing, basements, walls, facades, greenhouses, sun protection, garden fencing, wood protection, tent roof material, antifouling marine protection, fabrics; sanitary: public conveniences, bathrooms, shower curtains, toilet items, swimming pools, saunas, jointing, sealing compounds; requisites for daily life, machines, kitchen, kitchen items, sponge pads, recreational products for children, packaging for food or drink, milk processing, drinking water systems, cosmetics; machine parts: air conditioning systems, ion exchangers, process water, solar-powered units, heat exchangers, bioreactors, membranes (including but not limited to, membranes utilized in filtration devices such as ultrafiltration, microfiltration, and nanofiltration devices); medical technology: contact lenses, bandages, diapers, membranes, implants; consumer articles: automobile seats, clothing (socks, sports clothing, and the like), hospital equipment, door handles, telephone handsets, public conveyances, animal cages, cash registers, carpeting, wallpapers; boat hulls, docks, buoys, drilling platforms, ballast water tanks construction; and the like.

The presently disclosed and claimed inventive concept(s) also provides for the use of the biocidal compositions of the presently disclosed and claimed inventive concept(s) in producing hygiene products or items for medical technology. Examples of hygiene products of this type include, but are not limited to, toothbrushes, toilet seats, combs, bandages, medical devices, plastics, waxes, sanitary items, packaging materials, as well as any article which can come into contact with many people, for example but not by way of limitation, telephone handsets, stair rails, door handles, window catches, and also grab straps and grab handles in public conveyances. Examples of items for medical technology include, but are not limited to, bandages, catheters, adhesive tapes, tubing, cellulose pads, protein pads, carbohydrate pads, contact lenses, membranes, membrane spacers, implants, protective or backing films, surgical instruments, and the like.

In certain embodiments of the presently disclosed and claimed inventive concept(s), the effective amount of the selenium compound is in a range of from about 0.01 micrograms to about 100 micrograms of elemental selenium per square centimeter of surface area. In another embodiment of the presently disclosed and claimed inventive concept(s), the biocidal compositions are particularly effective against both gram negative and gram positive strains of bacteria and possess a broad spectrum of inhibition against many gram negative and gram positive strains (and including biofilms formed therefrom). A non-limiting example of a gram negative strain against which the biocidal composition is effective is *Pseudomonas aeruginosa*. A non-limiting example of a gram positive strain against which the biocidal composition is effective is *Staphylococcus aureus*. The biocidal compositions may also be particularly effective against viruses, fungi, algae, and mold.

The presently disclosed and claimed inventive concept(s) is also related to a thermoplastic polymer masterbatch composition that includes any of the biocidal compositions disclosed herein above uniformly dispersed in at least one of any of the thermoplastic polymers described herein above. The amount of the grafted biocidal composition may range from about 1% to about 20% by weight of the masterbatch composition, such as but not limited to, a range from about 5% to 15% by weight of the masterbatch composition. In certain embodiments, the biocidal composition may be added during thermal processing through a twin screw extruder such as that the biocidal composition is added to the molten plastic and mixed before extrusion for use directly or as the masterbatch composition.

The presently disclosed and claimed inventive concept(s) is also related to a method of producing an anti-microbial substrate by incorporating any of the biocidal compositions described herein above into any of the substrates described herein above. In this manner, the biocidal composition is disposed on the surface of the substrate and/or impregnated throughout the substrate. In one non-limiting embodiment, the method involves the incorporation of the biocidal composition within a molten plastic. The molten plastic is then allowed to harden to form a plastic material, wherein the biocidal composition is impregnated throughout the plastic material such that the biocidal composition remains attached to the plastic material. When the selenium compound comes into contact with a surface of the microbe, the selenium anion Se— and free radical species are generated. The selenium anion Se-remains attached to the surface of the plastic material, while the free radical species inhibits the proliferation of the microbe and thus inhibits growth of the microbe on the plastic material.

The presently disclosed and claimed inventive concept(s) is further related to a method of inhibiting the proliferation of microbes in or on a subject. In the method, any of the anti-microbial substrate compositions described herein above is disposed in or on the subject. When the substrate comes into contact with a surface of a microbe, the selenium anion Se— and free radical species are generated; the selenium anion Se— remains attached to the substrate, and the free radical species inhibits and/or inactivates the microbe, thereby inhibiting proliferation of the microbe on the substrate (including the inhibition of the formation of biofilms). In addition, the selenium anion Se— remains attached to the surface of the substrate after generation of the selenium anion Se— and the free radical species, such that the selenium anion Se— can continually generate additional free radical species when brought into contact with additional microbes.

The presently disclosed and claimed inventive concept(s) provides a new bacterialcidal and viralcidal grafting agent. The presently disclosed and claimed inventive concept(s) also provides a methodology to use of the aforementioned free radical technology as bacterialcidal or viralcidal agents. The presently disclosed and claimed inventive concept(s) further provides a method for directing the localized production of superoxide and descendant species thereof for selective destruction or modification of cells, tissue, membranes or extracellular fluids to combat a variety of localized problems, from infections, to cancer, to post surgical clotting and fibrosis.

The presently disclosed and claimed inventive concept(s) also provides a new biocidal grafting agent for addition to one of many different types of plastics during the manufacturing process. Such processes often employ thermoplastic resins that are melted, and the resultant molten matrix assumes the shape of the container as it cools. Another embodiment of the presently disclosed and claimed inventive concept(s) provides a method for directing the localized production of superoxide and descendant species thereof for selective destruction or modification of cells, tissue, membranes or extracellular fluids to combat a variety of localized problems, from infections and scarring around implantable devices to biofouling within tubing or on other products.

The impregnation of the biocidal composition such that it is dispersed throughout the material is particularly valuable in high risk environments known for nosocomial infective transfer like a hospital. Biocidal compositions impregnated throughout a substrate have the further benefit that a portion of a surface of the substrate could be mechanically removed adventitiously (i.e., mechanically degraded), while the substrate will possess antimicrobial activity and thus still function as intended, so it would not be immediately replaced. In this instance, if the grafting agent was only on the surface of the substrate, the mechanical degradation of the surface would reveal an area on which microbes could colonize. However, the presently disclosed and claimed inventive concept(s) allows for partial removal of a surface layer, as such removal only reveals fresh biocidal composition that is as efficacious against microbes as a new material.

An interesting discovery of the presently disclosed and claimed inventive concept(s) is that the tissue, cell or bodily fluid provides the reducing power for the generation of superoxide ($O_2._$). However, should additional reducing power be needed in vivo it can be supplied by exogenous glutathione or cysteine according to known techniques.

The attachment of biocidal compositions of the configurations described above to tubing, devices, or other plastic material, when presented to either endogenous thiols, such as glutathione which occurs in all aerobic living cells, or exogenous thiols, such as glutathione or cysteine, produces superoxide ($O_2^-$), hydrogen peroxide, the hydroxyl radical (.OH) and other cytotoxic reactive oxygen species so as to collectively form a localized free radical pharmacology based upon the catalytic selenium anion, RSe— Because superoxides are so deadly to cells, the body has natural mechanisms to destroy the superoxides, i.e., with superoxide dismutase. Thus, the superoxide radical, $O_2^-$, has a relatively short half life and will degrade. $H_2O_2$ and .OH are secondarily produced and are slightly longer lived. As used herein, for brevity, superoxide will include $O_2.^-$ and its descendent oxygen species. Because of the short life, $O_2^-$ must be generated at or near the site of intended destruction. The covalent attachment of selenium compounds which produce the RSe— anion provide for a new analytical chemistry based upon the generation and detection of superoxide ($O_2.$) using chemiluminescence or the reduction of various dyes, such as methylene blue or cytochrome C. Methylene blue and cytochrome C in the oxidized form may be reduced by selenium attached to a receptor molecule, through the generation of superoxide. The amount of reduced methylene blue or cytochrome C can be measured spectrophotometrically and quantitated, thereby reflecting the concentration of the molecule to which selenium is attached.

The non-metal element selenium exists in several catalytic and non-catalytic oxidation states, in vitro and in vivo. If present in sufficient concentrations of thiol compounds, selenium compounds such as selenides, RSe—, oxidize thiols, producing superoxide ($O_2^-$) and other biologically reactive oxygen species. Superoxide and the other produced reactive products, hydrogen peroxide, thiol radicals and other organic free radicals are toxic to biological membranes, molecules and cells. When present in sufficient concentration as the selenoselenide anion, RSe⁻, selenium can arrest and kill normal cells, cancer cells, bacterial cells, yeast cells and viruses. When organic selenium compounds are covalently attached to any targeting molecule such as a mono- or polyclonal antibody, peptide or polypeptide, hormone, vitamin, drug, or device, such conjugates comprise a new class of pharmaceuticals and devices that produce free radicals. Selenium is uniquely different from other elements that produce free radicals, i.e., iron, copper or cobalt, in that selenium can readily form small adducts replacing sulfur and it covalently combines with carbon and hydrogen compounds. Such selenium labeled adducts of the proper chemistry will remain non-toxic until activated by a thiol and the free radical pharmacology can be molecularly localized by the carrier molecule. This free radical chemistry is also useful for competitive protein binding assays. The free radical chemistry generated by selenium compounds can be detected by chemiluminescence or reduction of dyes, such as but not limited to methylene blue, by a spectrophotometer providing for quantitation of a compound which binds the antibody, hapten or drug to which selenium is attached and to which it subsequently reacts with thiols.

The biocidal compositions of the presently disclosed and claimed inventive concept(s) are applied to a target site or target molecule, or surgically implanted at a target site, whereupon superoxide ($O_2.$) is generated when the Se-carrier conjugate reacts with endogenous thiols on the surface of the targeted local tissue, bacteria, virus, protozoa or other targeted compounds. The selenium toxicity produced by the RSe— composition is very localized because it requires that a surface of a species of interest be available for interaction with the RSe— anion. The selenium compositions of the presently disclosed and claimed inventive concept(s) can be used to inhibit the proliferation of (i) all viruses of all plant, animal or human origin; (ii) all bacteria of all plant, animal or human origin; (iii) all protozoans of all plant, animal or human origin; and (iv) other pathogens. The selenium compositions of the presently disclosed and claimed inventive concept(s), for example, when available at the surface of the virus, bacteria, protozoa or cancer cells, will catalyze the production of superoxide, $H_2O_2$ and other reactive oxygen species. Viruses have surface proteins to which the selenium compositions of the presently disclosed and claimed inventive concept(s) may bind or come into close proximity. The selenium reacts with thiols in those surface proteins to generate the superoxide on the surface of the virus. The lack of an uptake mechanism in the virus is not important because the damage is done at the viral or cell surface.

The selenium compounds of the presently disclosed and claimed inventive concept(s) may be non-covalently attached to any solid or stationary matrix such as a cellulose pad, protein pad, other carbohydrate pad, plastic or other polymer matrix, such as but not limited to, rayon, nylon or polyester; or a biocompatible matrix for the purpose of generating superoxide ($O_2^-$) and its descendent reactive oxygen species when available to a surface of a species of interest. The device need not be metallic, but may be an organometallic compound or a metal coated with an organo compound to which the selenium compound can attach. The selenium non-covalently attached to the insoluble matrix inhibits cell growth in the localized area of the matrix due to the localized generation of superoxide.

In one aspect, the presently disclosed and claimed inventive concept(s) provides a method of treating or preventing growth of a species of interest through contact of a subject with a biocidal composition as described in detail herein, wherein the selenium composition comprises an inorganic or organic selenium compound, or formulation thereof, capable of generating superoxide radicals in the presence of a species of interest. The superoxide radicals generated by the inorganic or organic selenium compound inhibit or inactivate an agent of the species of interest and thereby treat or prevent growth of the species of interest in or on the subject.

In another aspect, the presently disclosed and claimed inventive concept(s) provides a method of treating or preventing the development or transmission of a species of interest in or on a subject through the use of a biocidal composition comprising a selenium composition as described in detail herein, wherein the selenium composition comprises an organic selenium compound, or formulation thereof, capable of generating superoxide radicals in the presence of a species of interest. The method involves providing the biocidal composition capable of generating superoxide radicals in the presence of an infectious agent, and applying an effective amount of the biocidal composition to the subject. The superoxide radicals generated by the organic selenium compound inhibit or inactivate the species of interest and thereby treat or prevent the growth or transmission of the species of interest in the subject.

In a further aspect, the presently disclosed and claimed inventive concept(s) provides biocidal compositions having, on at least one surface thereof, an effective amount of an inorganic or organic selenium compound, or formulation thereof, capable of generating superoxide radicals in the presence of a species of interest or reduced thiol compound or other electron donating group. The organic selenium compound may be covalently or non-covalently associated with the composition, and an effective amount of the organic selenium compound, or formulation thereof, is retained on or available to a surface of the composition when the composition is in contact with a subject.

In particularly useful embodiments of the biocidal compositions of the presently disclosed and claimed inventive concept(s), the effective amount of the organic selenium compound, or formulation thereof, that is retained on or available to a surface of the composition when such composition is in contact with the subject is sufficient to inhibit or inactivate an agent of infectious disease or other undesired cell(s).

In other embodiments, the organic selenium compound, or formulation thereof, does not comprise a thiol group or a thiol-containing compound. In particular embodiments, the organic selenium compound, or formulation thereof, does not comprise glutathione.

In further embodiments, the subject is a mammal. In particular embodiments, the subject is a human.

In particularly useful embodiments, at least about half of the elemental selenium from the organic selenium compound, or formulation thereof, exists in an active state that is capable of generating superoxide radicals in the biocidal composition. In further particular embodiments, the biocidal composition has between about 0.01 µg and about 100 µg of elemental selenium per square centimeter of surface area. In further useful embodiments, the biocidal composition has between about 1 µg and about 10 µg of elemental selenium per square centimeter of surface area. In yet further particular embodiments, the biocidal composition has between about 5 µg and about 6 µg of elemental selenium per square centimeter of surface area.

EXAMPLES

The following examples serve to illustrate certain useful embodiments and aspects of the presently disclosed and claimed inventive concept(s) and are not to be construed as limiting the scope thereof. Alternative materials and methods can be utilized to obtain similar results.

Example 1

General Procedure for the Production of Thermally Grafted Organoselenium Compounds with Thermoplastics Thermoplastic resin pellets were obtained from commercial sources. Generally, broad classes of thermoplastic resins were chosen with melting points ranging from 170° C. to 250° C. and with melt flow indexes ranging from 2 g/10 min to 1600 g/10 min. Resin families included polyolefins (such as polypropylene (PP), polyethylene (PE), PP/PE copolymers, and LLDPE), PVC, and polystyrenes (such as ABS), and urethanes. Pellets were weighed to obtain a mass of 100 g. The organoselenium compound, for example, diselanediylbis (2-hydroxypropane-3,1-diyl)bis(2-methylacrylate), was weighed to achieve a loading by weight. Mass compositions of the compound were added in ranges of 0.25% to 4%. Once the organoselenium compound was added to the pellets, the mixture was homogenized with an overhead stirrer, resulting and an adsorbed coating. The resin pellets were placed in an injection molder, and the coated pellets were melt extruded, obtaining a plaque through which the organoselenium compound becomes covalently grafted to the molten polymer. Once the plaques reached room temperature, they were tested for microbiology.

Example 2

Microbiology Obtained from Plagues Using Polypropylene

PP resin pellets were treated with an organoselenium agent dosed at 1% wrt to elemental selenium, 2.81% organoselenium compound. The plaques were obtained by injection molding at 235° C. FIG. 1 shows that the organoselenium plaques showed 5.4 logs of inhibition against *Staphylococcus aureus* versus control.

Possible Modifications to Established Protocols: This intuitive gap can be overcome with a set of simple procedural changes that can be applied to most anti-biofilm assays. Namely, after the growth period, any material other than the test article is removed and discarded and any non-attached cells are removed by gently rinsing the test article. This modification leaves behind the more strongly bound biofilm, which is then tested as usual. This will not work on some assays, such as Zone of Inhibition, which should not be used for non-leeching technologies.

Assays Utilized to Measure Selenium Activity:

The following assays have been utilized to measure selenium activity of various substrates:

1) Chemiluminescent Selenium Activity Assay:

Overview:

This assay detected the presence of superoxide produced from the catalytic cycle with organoselenium-enabled substrates and glutathione.

Positive Result:

A luminometer was used to measure RLU's (Relative Light Units) resulting from the chemiluminescence generated by the superoxide oxidation of lucigenin. Typical results produced a positive signal greater than 100× relative to the background count.

2) Bacterial Inhibition Assay:

Overview:

This colony forming unit (CFU) assay is optimized for *Staphylococcus aureus* and measures the bacterial attached to a substrate surface.

Positive Result:

An incubated rinse from the substrate was serially diluted, then plated for count of CFUs. Colonies were counted versus positive, negative, and substrate controls. The bacterial inhibition was compared to controls. A Log 10 value was reported for each control and substrate. Typically, values of 4 Logs of inhibition were considered highly antimicrobial. Below 2 Logs was considered marginal and usually drives material optimization and dosing responses for a specific material.

Negative Result:

A CFU assay with total inhibition on an active organoselenium-enabled substrate produces zero colony forming units.

3) Scanning Electron Microscopy: (SEM) Analysis:

Overview:

For microbes whose physiological make-up does not allow consistent growth in the plate assay similar to *Staphylococcus aureus*, Scanning Electron Microscopy (SEM) was used to image a surface.

Positive Result:

Although qualitative, images produced the ability to assess the quality of a biofilm growth and the approximate bacteria count present. Images were high resolution and useful for marketing.

Negative Result:

A highly active organoselenium-enabled substrate showed no visual evidence of active bacteria or established biofilms.

4) Stability through Colony Forming Unit (CFU) Assay:

Overview:

Accelerated stability studies were performed by incubation at 67° C. where 1 week at the elevated temperature is commonly accepted to approximate 8 weeks at physiological conditions. Note that some substrates may not be stable at this temperature and this assay may not be meaningful for all substrates.

Positive Result:

Incubation of active substrates at elevated temperatures produced CFU assay results under the Bacterial Inhibition Assay described above that demonstrated 4 Logs of bacterial inhibition or greater.

5) Confocal Laser Scanning Microscopy:

Overview:

Confocal Laser Scanning Microscopy is a lower resolution imaging technique that was used to gather quantitative data on microbial inhibition. Lux or GFP plasmids are inserted into the bacterial strain such that they fluoresce under the microscope, and are only visible when they are alive.

Positive Result:

The confocal imaging system allows "slices" to be taken and added together in a separate computer program to provide a three dimensional representation of the biofilm. The amount of light produced is consistent between cells of the same species, and separate genes can be inserted into separate organisms, allowing two component biofilms to be imaged and quantified.

Negative Result:

A highly active surface will appear as a simple black image.

Figure 3:
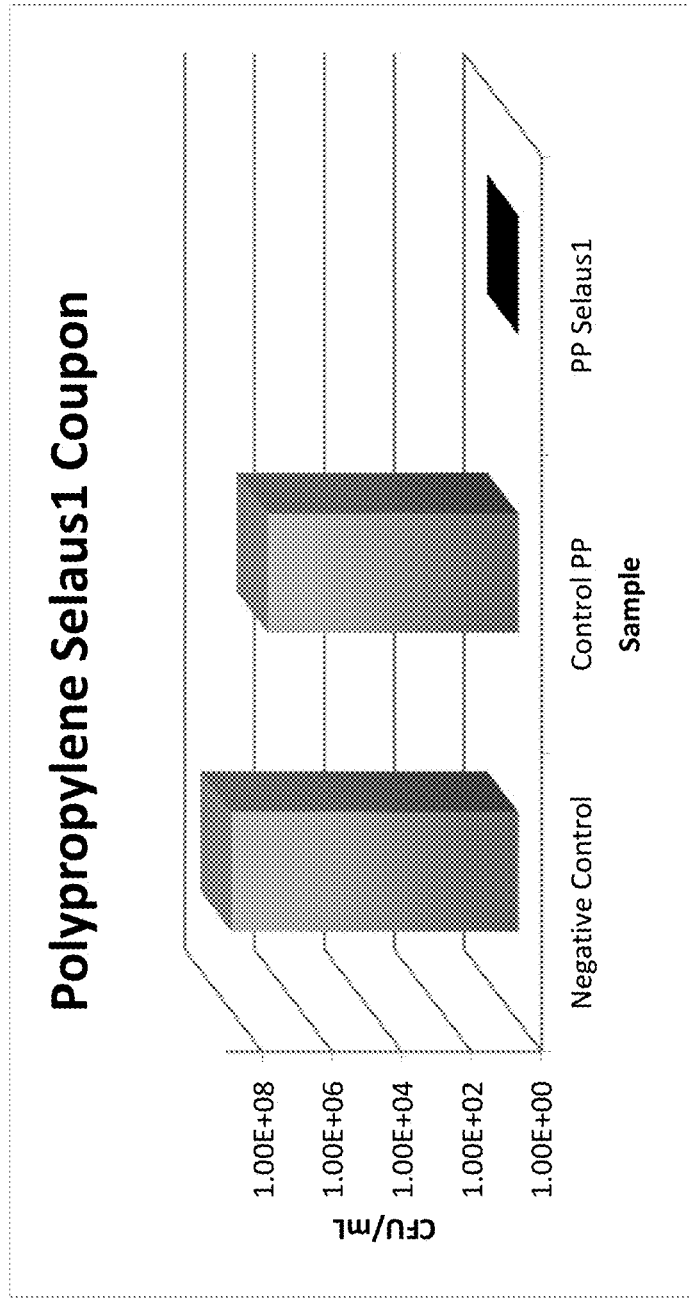
FIG. 3 graphically illustrates the effect of the organoselenium compound on the inhibition of in vitro development of *Staphylococcus aureus* biofilm on a polypropylene coupon doped with the organoselenium compound.
Figure 4:
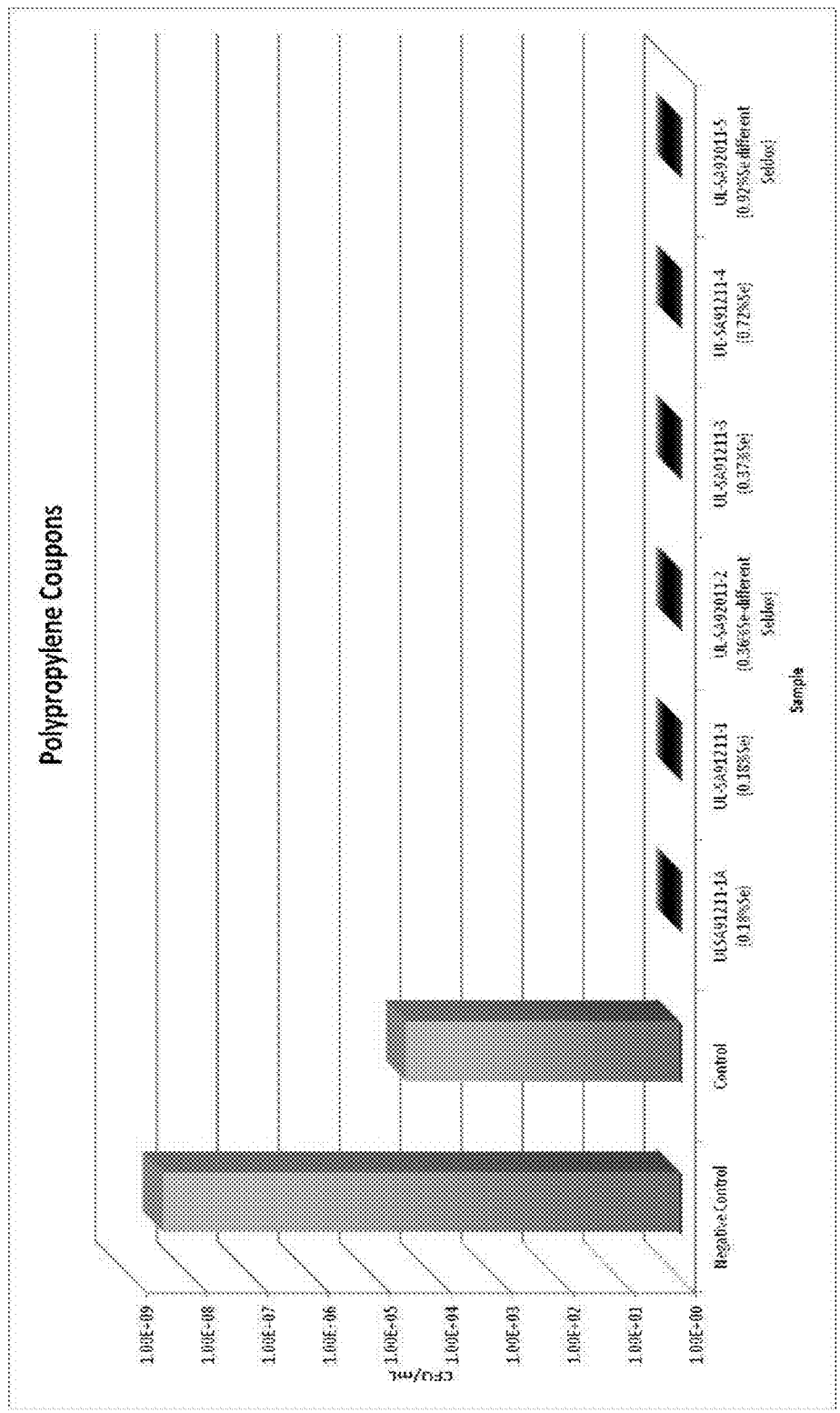
FIG. 4 graphically illustrates the effects of the organoselenium compound on the proliferation of *Staphylococcus aureus* on various polypropylene coupons dosed with the organoselenium compound and formed by melt processing at 235° C.

Data Summary on Organoselenium-Enabled Polypropylene:

The results from the microbiological colony forming unit assays and a stability study of polypropylene materials are shown in FIGS. 3-4 and summarized in Table I.

TABLE I

| Organoselenium-enabled PP | Logs of Inhibition vs. *S. aureus* |
|---|---|
| 1% Se | 7.927 |
| 8 week equivalent | 7.770 |

Figure 2:
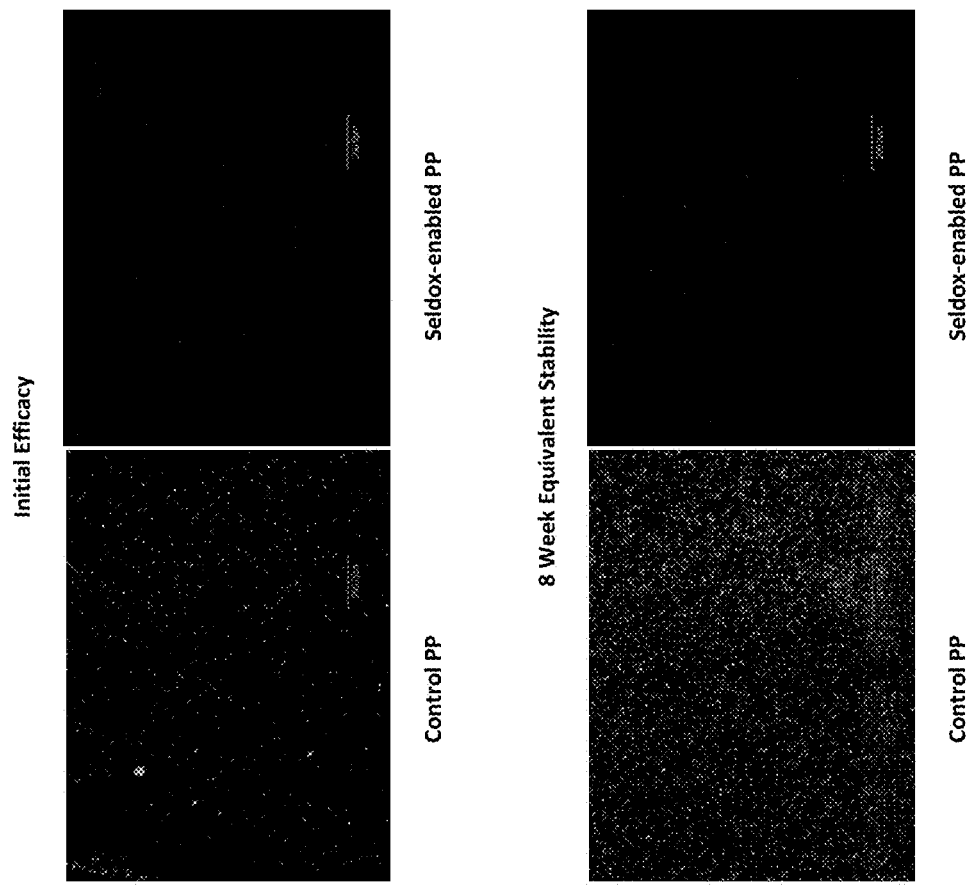
FIG. 2 contains confocal laser scanning microscopic images of a stability study of a polypropylene surface enabled with the organoselenium compound upon challenge with *Staphylococcus aureus*.

In addition, imaging studies were performed via confocal laser scanning microscopy (CLSM); the results of these studies are shown in FIG. 2. Total selenium was measured in order to quantify the amount of selenium in the material, and the amount that leached into the solution under challenge conditions (one week in PBS at 67° C.). The results showed that 13.1 μg of selenium leached into the water during the challenge, approximately 1% of the total in the material. This material has not been optimized for stability due to the proposed application.

Figure 5:
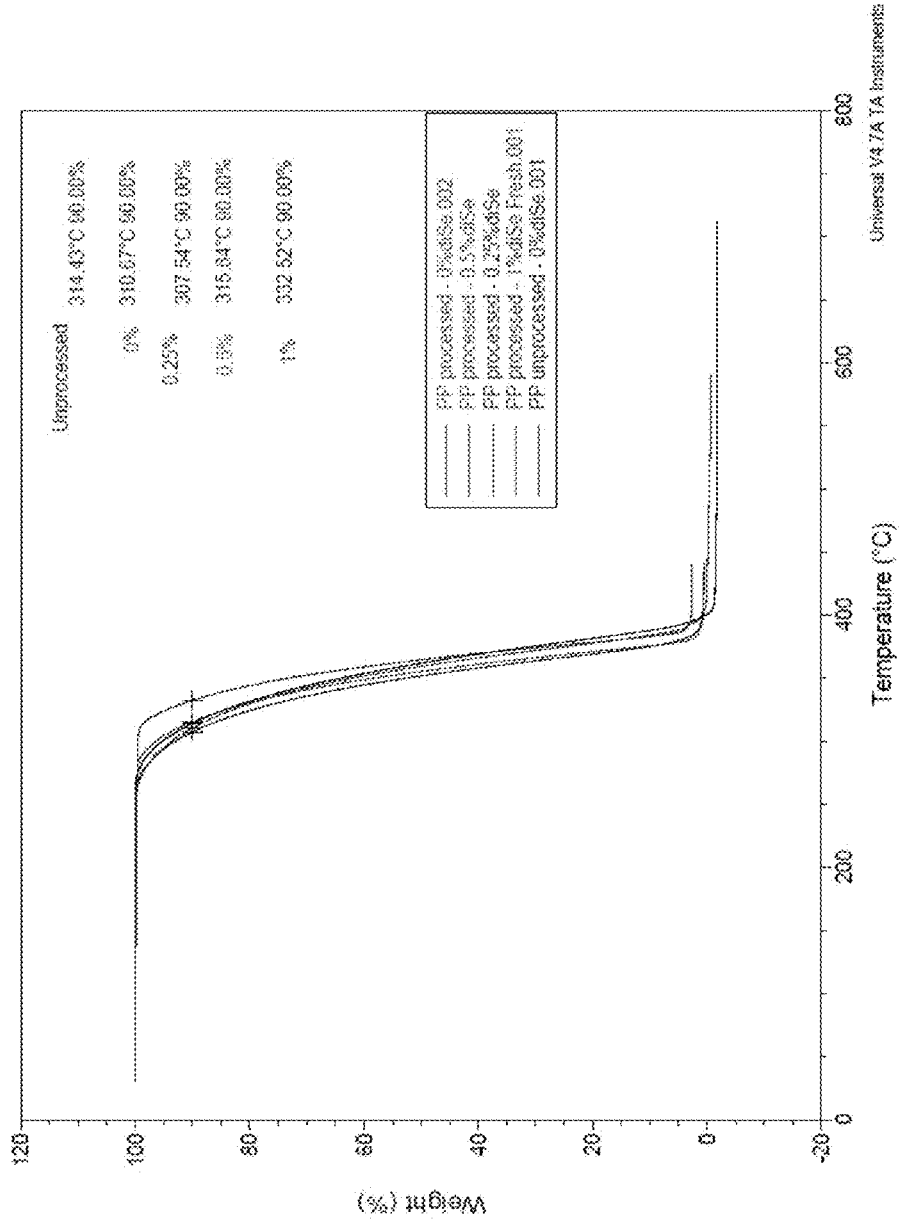
FIG. 5 graphically illustrates the mechanical properties of polypropylene loaded with various concentration percentages of the organoselenium compound.
Figure 6:
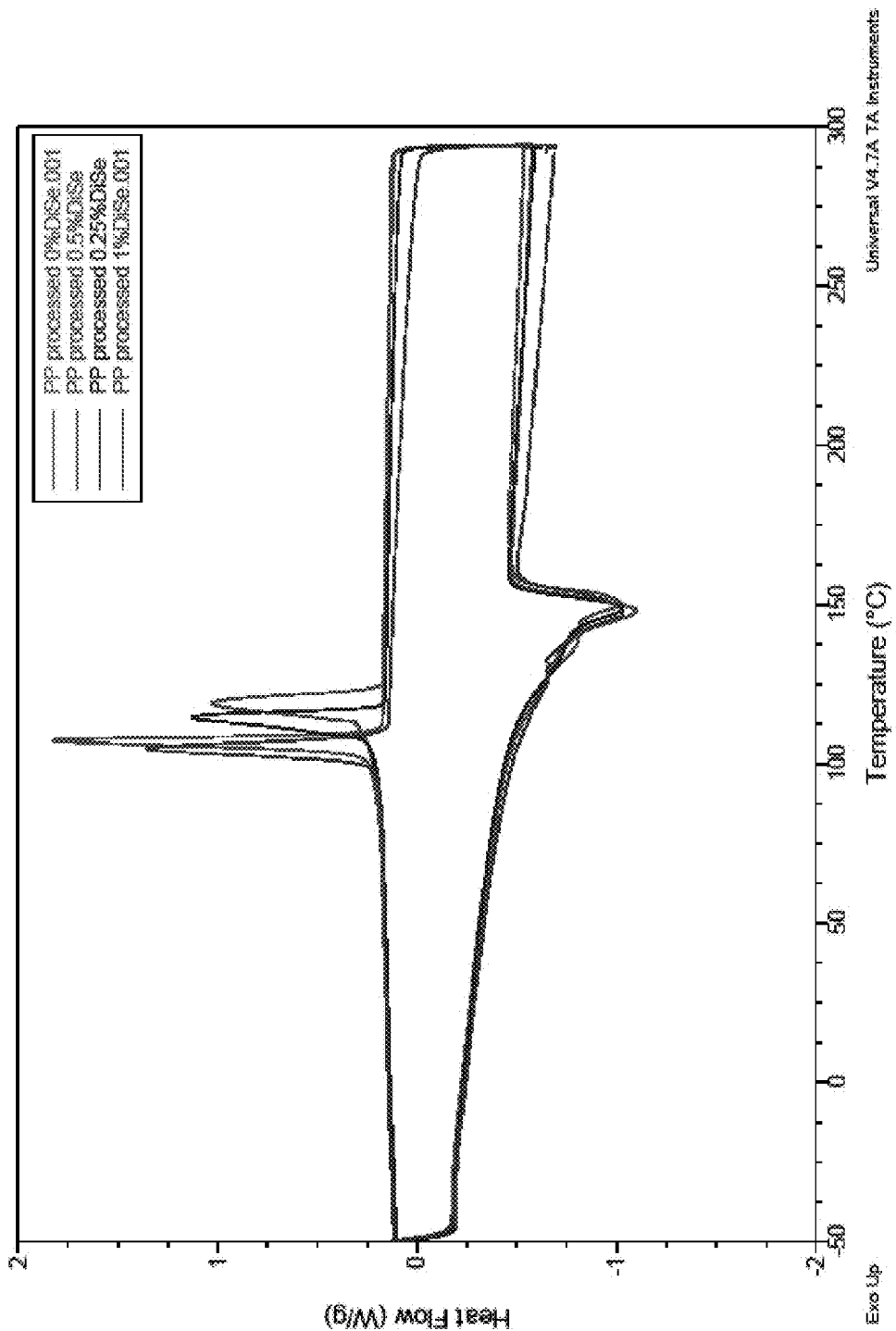
FIG. 6 graphically illustrates the thermal properties of polypropylene loaded with various concentration percentages of the organoselenium compound.
Figure 7:
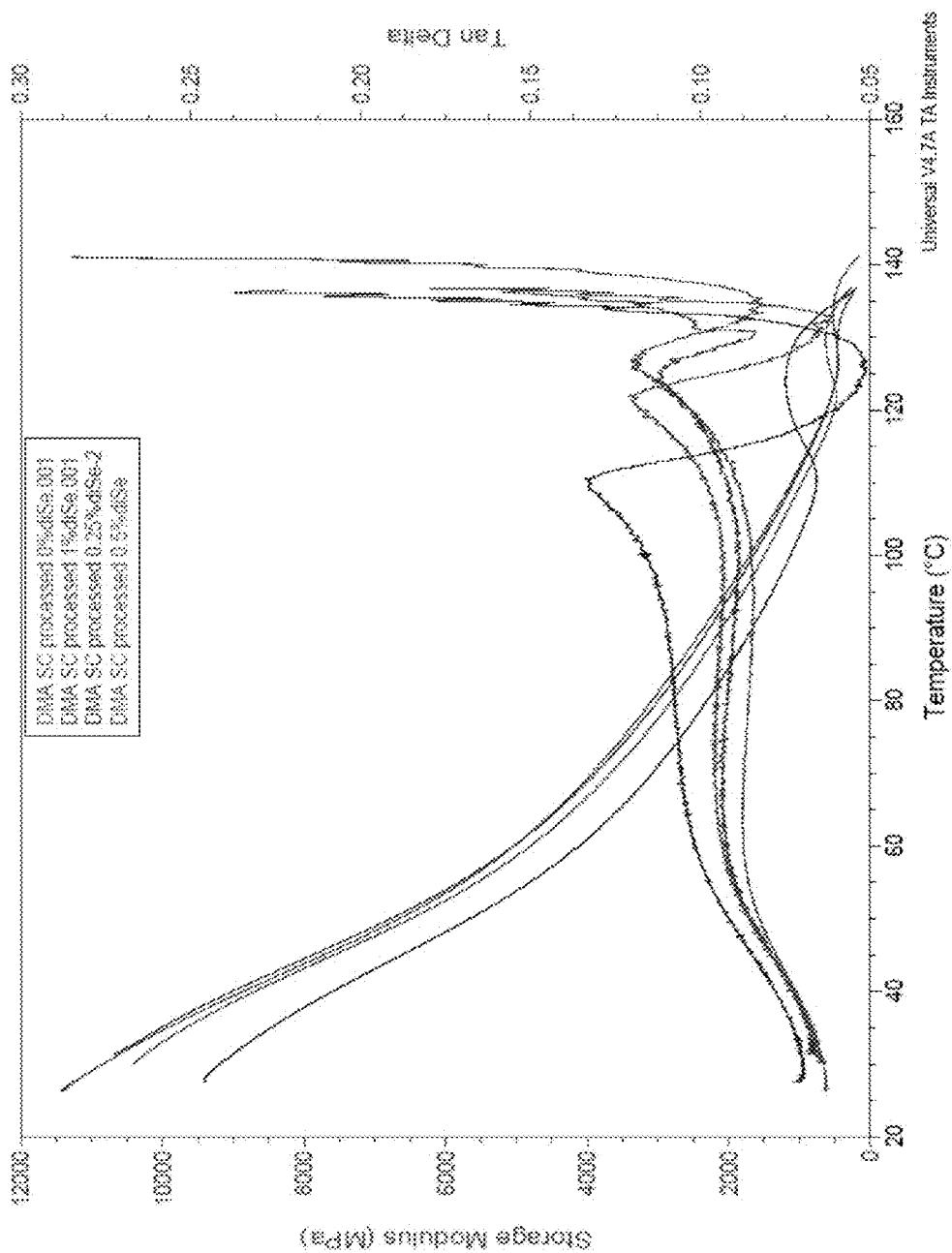
FIG. 7 graphically illustrates a Dynamic Mechanical Analysis (DMA) of polypropylene loaded with various concentration percentages of the organoselenium compound.

Further, physical characteristics data was generated for a dose response of organoselenium-polypropylene (PP), in the form of Thermogravimetric Analysis (TGA), Dynamic Mechanical Analysis (DMA), and Differential Scanning calorimetry (DSC). Doses tested included 0% (control), 0.25%, 0.5%, and 1% organoselenium compound. These results, as illustrated in FIGS. 5-7, show the addition of organoselenium to polypropylene did not significantly alter the thermal stability or mechanical property of the native polymer. In particular, FIG. 5 shows that TGA indicates that addition of organoselenium has no appreciable effect on the thermal properties of the polypropylene; FIG. 6 indicates that the addition of organoselenium has no appreciable effect on the thermal properties of polypropylene; and FIG. 7 shows that DMA indicates that the addition of organoselenium has no appreciable effect on the mechanical properties of the polypropylene.

Example 3

Microbiology Obtained from Plaques Using ABS

Figure 8:
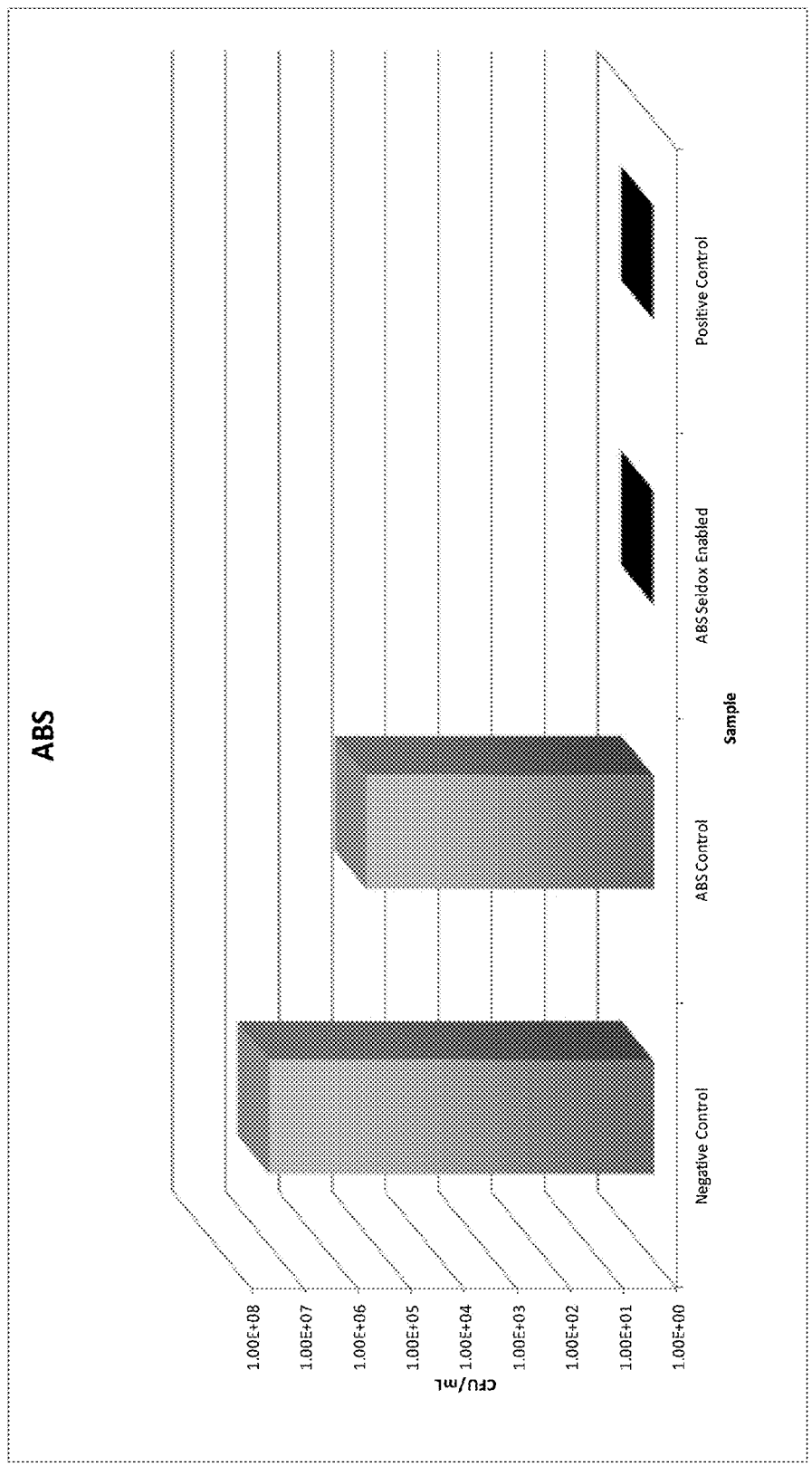
FIG. 8 graphically illustrates the effect of the organoselenium compound on the inhibition of development of *Staphylococcus aureus* on plaques formed from ABS resin pellets treated with the organoselenium compound.

ABS resin pellets were treated with an organoselenium agent dosed at 1% wrt to elemental selenium, 2.81% organoselenium compound. Untreated polyester sample was used as a negative control, while treated titanium washer was used as a positive control. ABS samples were washed in DiH$_2$O 1× prior to being autoclaved. An additional wash with DiH$_2$O followed. The samples were tested against *Staphylococcus aureus* using SOP-001. FIG. 8 illustrates that the organoselenium plaques exhibited inhibition against *Staphylococcus aureus* similar to the other materials tested herein.

Example 4

Microbiology Obtained from Plaques Using Thermoplastic Polyurethane

Figure 9:
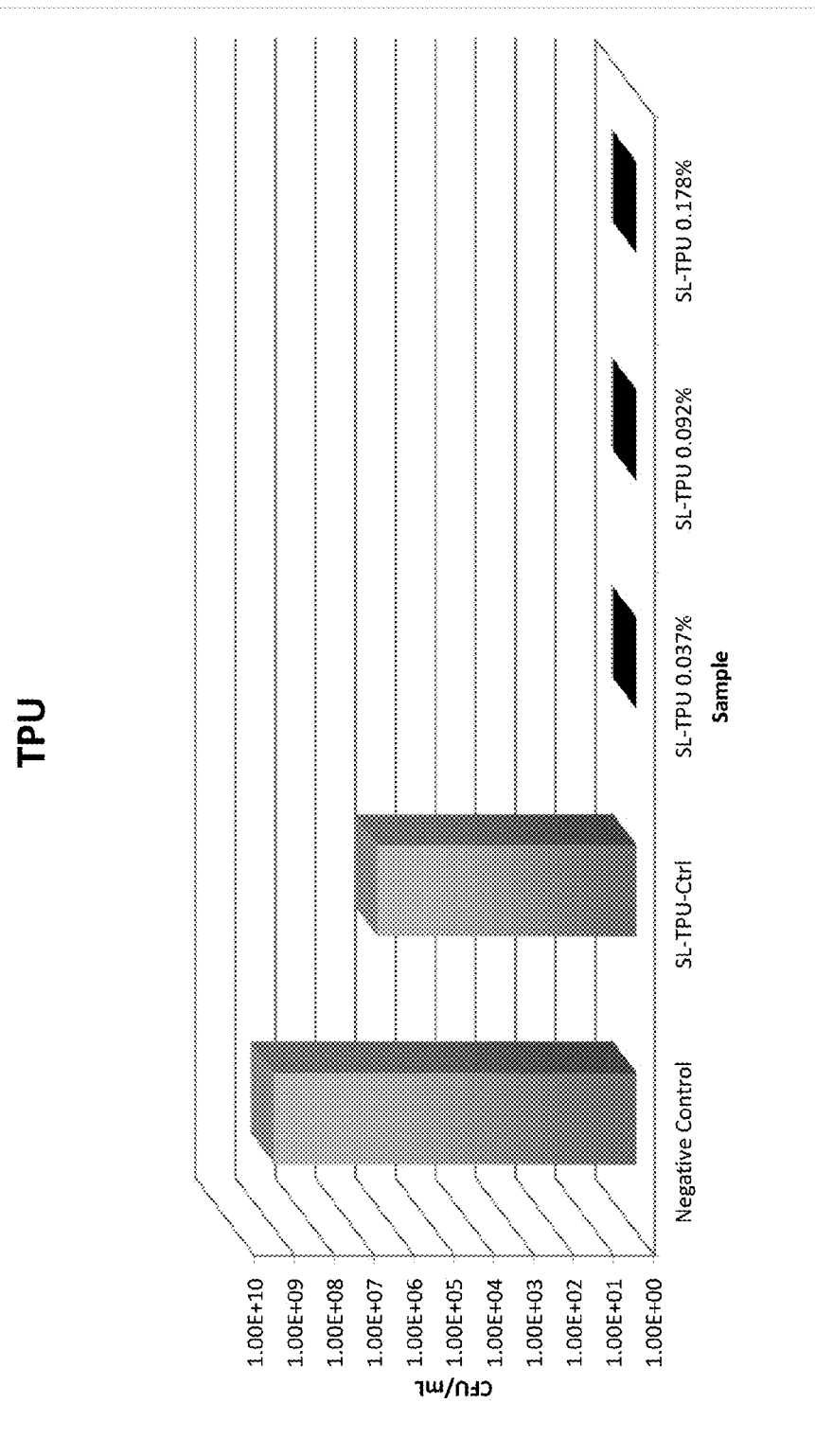
FIG. 9 graphically illustrates the effect of the organoselenium compound on the inhibition of in vitro development of *Staphylococcus aureus* on plaques obtained by injection molding of TPU resin pellets dosed with various concentration percentages of the organoselenium compound.

TPU resin pellets were treated with an organoselenium agent dosed at 0.037%, 0.092% and 0.178% wrt to elemental selenium, and 0.1%, 0.5%, 2.6% organoselenium compound. The plaques were obtained by injection molding at 235° C. The samples were tested against *Staphylococcus aureus*, and the results are shown in FIG. 9. The graph shows that the organoselenium plaques showed 6.4 logs of inhibition against *Staphylococcus aureus*.

Example 5

Figure 10:
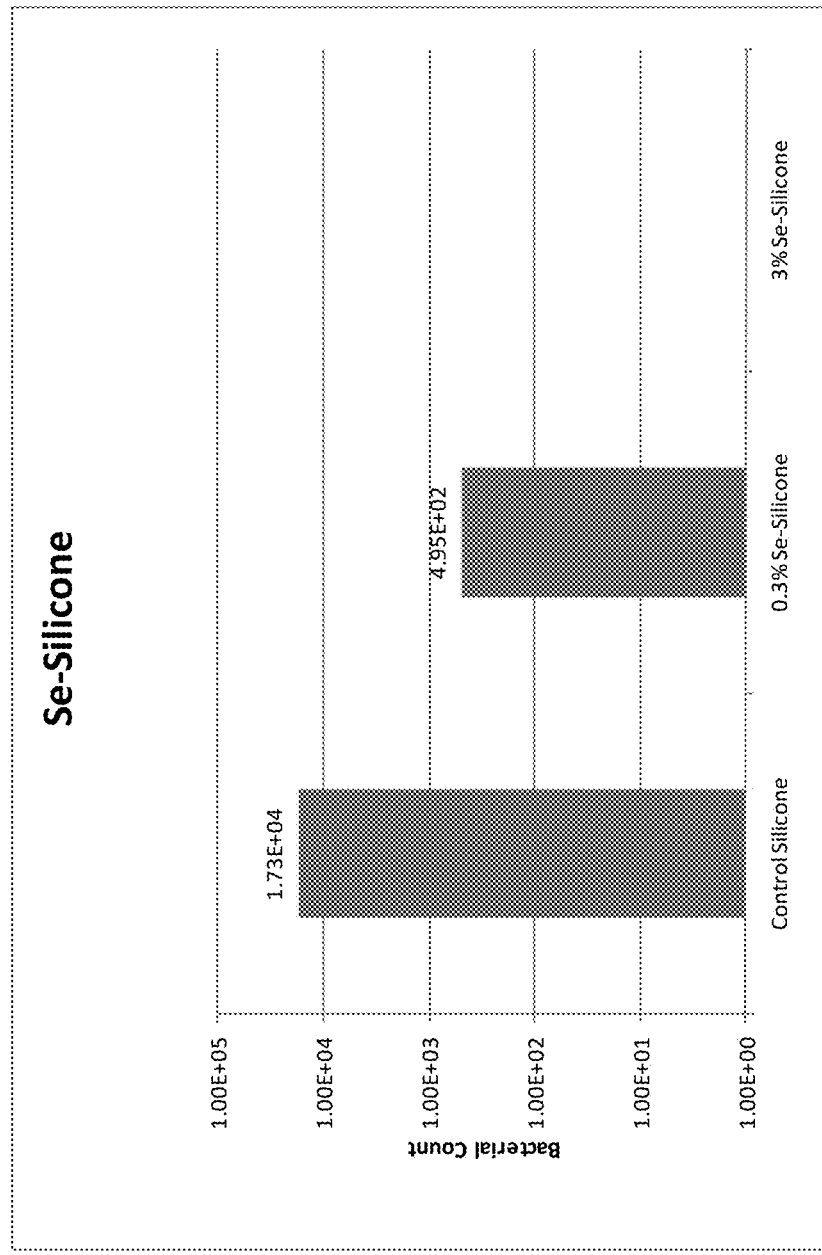
FIG. 10 graphically illustrates a dose response of the organoselenium compound doped into a commercial silicone.

Procedure for Co-Polymerization of an Organoselenium Compound and Silicone Monomers Commercial silicone sealant cured by moisture was doped with an organoselenium tetraol by mechanical mixing. The resultant mixture was allowed to cure. FIG. 10 shows a dose response of treated organoselenium compound doped into a commercial silicone versus control.

Example 6

Procedure for Obtaining a Masterbatch of Polypropylene

A high meltflow index polypropylene was doped with 5%, 10%, and 13% of the organoselenium compound, then placed in a twin screw extruder. The heating zones were 125, 140, 140 and 140° C., respectively. The screw speed was set to 150 rpm. The resultant thermally grafted polymer was extruded in thin strands, which were then chipped into pellets.

Example 7

Procedure for Obtaining Plagues Prepared from Virgin Resin and Masterbatch Resin Procedure for obtaining plaques prepared from virgin resin and masterbatch (MB) resin at 5%, 13% and 10% nominal loading. Each of these master batch concentrations were mixed with untreated polypropylene resin pellets to achieve an effective dosing of 2.81% organoselenium compound and 1% with respect to elemental selenium. The mixture was ground with a burr grinder to achieve a homogeneous mixture.

Selenium and control PP MB contact lens cases were washed in hexane overnight and twice in dH2O (30 min each). The samples were sterilized by dried autoclaving and washed in dH2O for 30 minutes. Each sample was then placed in each well of a 24-well polystyrene plate containing 1 ml of diluted TSB in PBS (1:24) supplemented with Erythromycin (1 μg/ml). Each well was then inoculated with about 100 cfu/ml of *S. aureus* GFP, and the plate was incubated at 37° C. for at least 24 hours. Each sample was gently washed in PBS to remove planktonic cells. Attached bacteria were removed by vortexing in 1 ml PBS, and the number of attached bacteria was determined by 1:10 serial dilution and plating on LB Agar plate. The bacteria attached to the PP MB contact lens cases were also visualized by CLSM.

Figure 11:
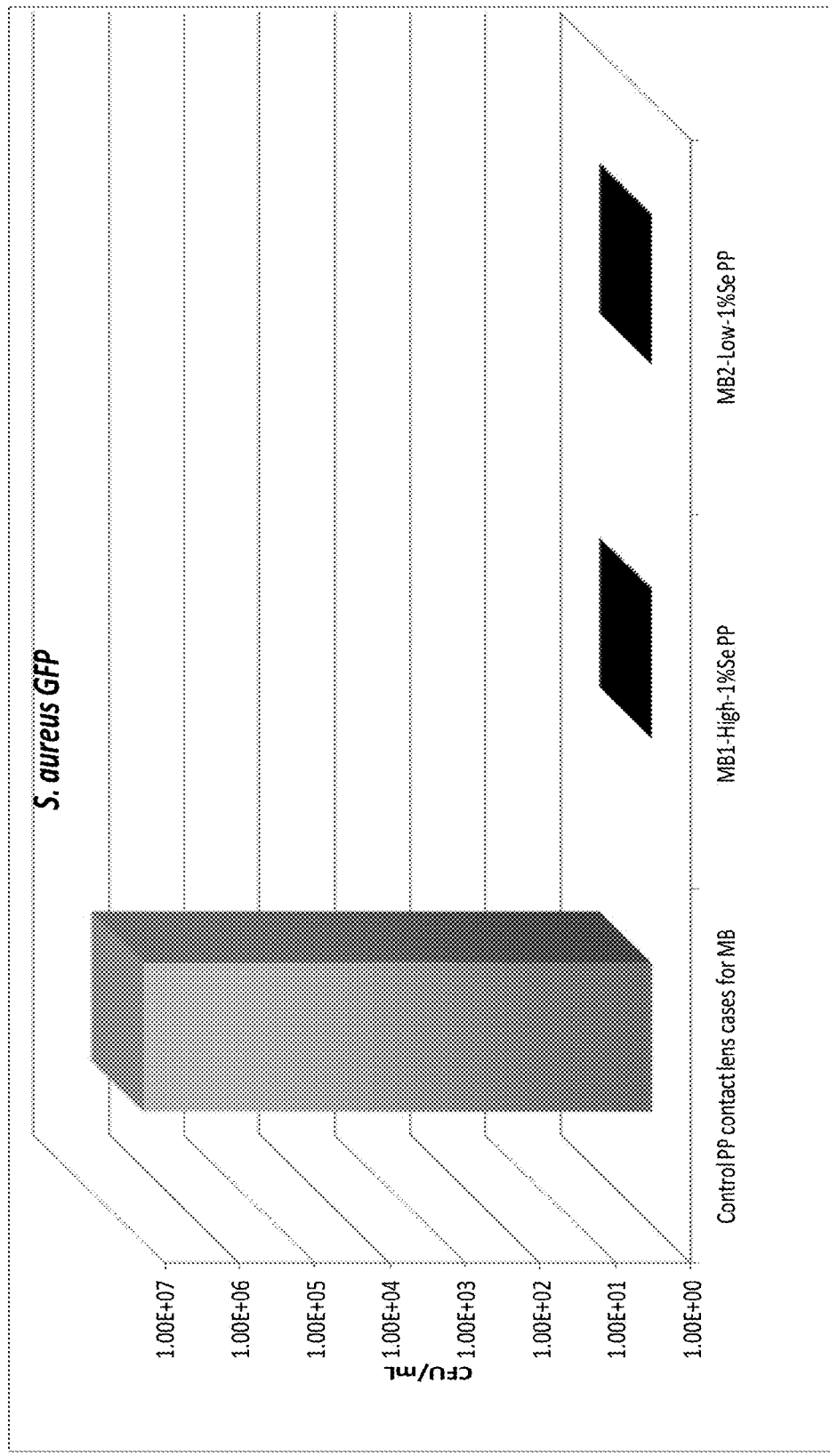
FIG. 11 graphically illustrates the effect of the organoselenium compound on the inhibition of proliferation of *Staphylococcus aureus* on masterbatch contact lens cases formed from masterbatch resin dosed with various concentration percentages of the organoselenium compound.
Figure 12:
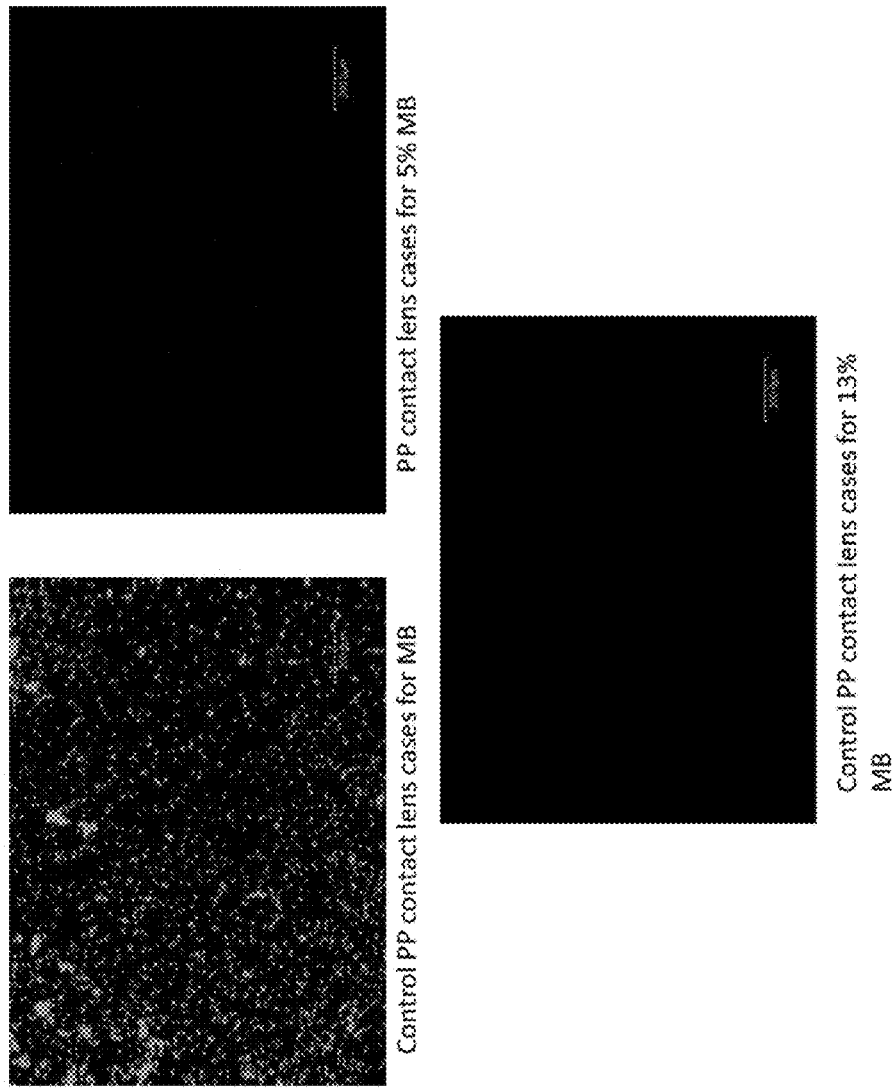
FIG. 12 contains confocal laser scanning microscopic images visualizing any bacteria attached to the masterbatch contact lens cases formed from masterbatch resin dosed with various concentration percentages of the organoselenium compound.

FIG. 11 shows that 6.8 logs of inhibition against *S. aureus* GFP was observed in the organoselenium-treated PP MB contact lens cases. FIG. 12 contains confocal microscopy images that show living *S. aureus* on the control, but no viable organisms on the organoselenium treated sample.

Figure 13:
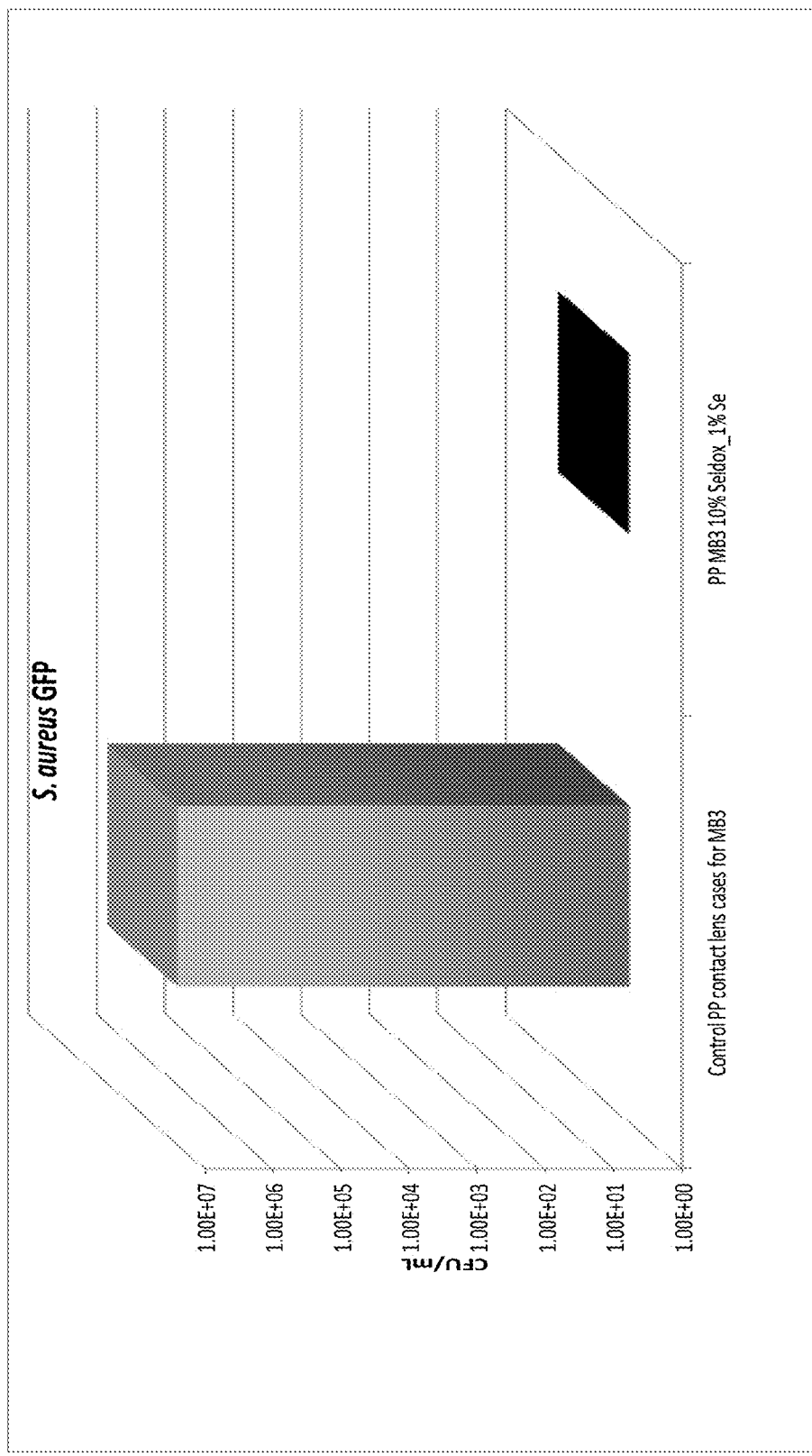
FIG. 13 graphically illustrates the effect of the organoselenium compound on the inhibition of proliferation of *Staphylococcus aureus* on masterbatch contact lens case formed from another masterbatch resin dosed with the organoselenium compound.

FIGS. 13-14 illustrate the results from a third organoselenium-treated PP MB contact lens case; FIG. 13 shows that 6.63 logs of inhibition against *S. aureus* GFP was observed in the organoselenium-treated PP MB contact lens case. FIG. 14 contains confocal microscopy images that show living *S. aureus* on the control, but no viable organisms on the organoselenium treated sample.

Thus, in accordance with the presently disclosed and claimed inventive concept(s), there has been provided a method of producing selenium-based biocidal formulations that fully satisfies the objectives and advantages set forth hereinabove. Although the presently disclosed and claimed inventive concept(s) has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

What is claimed is:

1. A composition, comprising:
    a substrate having a surface; and
    a biocidal composition disposed on the surface of the substrate and/or impregnated throughout the substrate, the biocidal composition comprising at least one of:
    (1) diselanediylbis(2-hydroxypropane-3,1-diyl)bis(2-methylacrylate); and
    (2) 3,3'-diselanediylbis(propane-1,2-diol).

2. The composition of claim 1, wherein the biocidal composition is permanently attached to the substrate, whereby the biocidal composition is substantially unable to leach from the substrate.

3. The composition of claim 1, wherein the biocidal composition is effective against at least one of a gram positive bacterial strain, a gram negative strain, a virus, a fungus, an algae, and a mold.

4. The composition of claim 3, wherein the biocidal composition is effective against at least one gram positive bacterial strain and at least one gram negative strain, wherein the gram positive strain is *Staphylococcus aureus* and the gram negative strain is *Pseudomonas aeruginosa*.

5. The composition of claim 3, wherein the biocidal composition is effective against at least one gram positive bacterial strain, at least one gram negative strain, at least one virus, at least one fungus, at least one algae, and at least one mold.

6. The composition of claim 1, wherein the biocidal composition inhibits formation of bacterial biofilms on the substrate.

7. The composition of claim 1, wherein the selenium compound of the biocidal composition is present in a range of from about 0.01 micrograms to about 100 micrograms of elemental selenium per square centimeter of surface area.

8. The composition of claim 1, wherein the selenium anion Se— and free radical species are generated when the biocidal composition comes into contact with a surface of a living cell and/or living organism, whereby the selenium anion Se— remains permanently attached to the substrate and the free radical species inhibits and/or inactivates said living cell and/or living organism, thereby inhibiting growth of the living cell and/or living organism on the substrate.

9. The composition of claim 1, wherein the substrate is a solid substrate formed of a thermoplastic polymer, and wherein the grafting agent of the biocidal composition covalently attaches to the thermoplastic polymer when the polymer is in a molten form.

10. The composition of claim 1, wherein the substrate is a semi-permeable substrate, and wherein the biocidal composition forms a covalent network within the semi-permeable substrate.

11. The composition of claim 10, wherein the covalent network formed by the biocidal composition is free of covalent bonds between the biocidal composition and the semi-permeable substrate, and wherein branches of the covalent network are interdigitated.

12. The composition of claim 10, wherein the biocidal composition covalently attaches to the semi-permeable substrate.

13. The composition of claim 1, wherein the substrate is a liquid substrate.

14. The composition of claim 1, wherein the substrate is selected from the group consisting of catheters, bandages, adhesive tapes, fabrics, fibers, plastics, cellulose pads, protein pads, carbohydrate pads, contact lenses, diapers, membranes, membrane spacers, implants, tubing, beverage tubing, medical tubing, paints, coatings, and combinations thereof.

15. A thermoplastic polymer masterbatch composition, comprising:
   a grafted biocidal composition uniformly dispersed in at least one thermoplastic polymer, the amount of the grafted biocidal composition ranging from about 1% to about 20% by weight, the grafted biocidal composition comprising at least one of:
   (1) diselanediylbis(2-hydroxypropane-3,1-diyl)bis(2-methylacrylate); and
   (2) 3,3'-diselanediylbis(propane-1,2-diol).

* * * * *